(12) United States Patent
Patterson et al.

(10) Patent No.: US 10,561,599 B2
(45) Date of Patent: Feb. 18, 2020

(54) METHODS AND KITS FOR TREATING CHEMICALLY RELAXED HAIR

(71) Applicant: L'OREAL, Paris (FR)

(72) Inventors: Kwana Patterson, Clark, NJ (US); Barbara Mitchell, Clark, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 170 days.

(21) Appl. No.: 15/604,152

(22) Filed: May 24, 2017

(65) Prior Publication Data

US 2018/0338901 A1 Nov. 29, 2018

(51) Int. Cl.
| | | |
|---|---|---|
| A61K 8/87 | (2006.01) | |
| A61Q 5/04 | (2006.01) | |
| A61K 8/36 | (2006.01) | |
| A61K 8/362 | (2006.01) | |
| A61K 8/41 | (2006.01) | |
| A61Q 5/06 | (2006.01) | |

(52) U.S. Cl.
CPC ............... *A61K 8/87* (2013.01); *A61K 8/36* (2013.01); *A61K 8/362* (2013.01); *A61K 8/41* (2013.01); *A61Q 5/04* (2013.01); *A61Q 5/06* (2013.01); *A61K 2800/48* (2013.01); *A61K 2800/54* (2013.01); *A61K 2800/594* (2013.01); *A61K 2800/884* (2013.01)

(58) Field of Classification Search
None
See application file for complete search history.

(56) References Cited

U.S. PATENT DOCUMENTS

| | | |
|---|---|---|
| 5,951,969 A | 9/1999 | Golinski et al. |
| 5,985,803 A | 11/1999 | Rizvi et al. |
| 9,095,518 B2 | 8/2015 | Pressly et al. |
| 9,326,926 B2 | 5/2016 | Pressly et al. |
| 9,597,273 B2 | 3/2017 | Pressly et al. |
| 2007/0107142 A1 | 5/2007 | Nguyen et al. |
| 2013/0149274 A1 | 6/2013 | Nguyen et al. |
| 2014/0171354 A1 | 6/2014 | Miralles et al. |
| 2015/0004117 A1 | 1/2015 | Tan et al. |
| 2015/0004119 A1 | 1/2015 | Tan et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0290101 A1 | 10/2015 | Pressly et al. |
| 2015/0328102 A1 | 11/2015 | Pressly et al. |
| 2016/0175238 A1 | 6/2016 | Shin et al. |
| 2016/0235649 A1 | 8/2016 | Streuli |
| 2017/0119122 A1 | 5/2017 | Rautenberg-Groth et al. |

FOREIGN PATENT DOCUMENTS

| | | | |
|---|---|---|---|
| EP | 0159628 A2 * | 10/1985 | ............ A61K 8/585 |
| JP | 63154611 A | 6/1988 | |
| JP | 2015086211 A | 5/2015 | |
| WO | WO-0152005 A1 | 7/2001 | |
| WO | WO-2016/100885 A1 | 6/2016 | |

OTHER PUBLICATIONS

International Search Report and Written Opinion dated Jul. 25, 2018 for corresponding PCT Application No. PCT/US2018/034366.
Anonymous: "Curly hair conditioner", Mintel, GNPD, 2015; pp. 1-2; XP002782449.
Olaplex with relaxers, OLAPLEX™, pp. 1-2, Apr. 11, 2017, https://olaplex.es/olaplex-with-relaxers/.
Relaxers, Resource Library, Olaplex Education, pp. 1-2, Apr. 11, 2017, https://help.olaplex.com/detail/relaxers.

* cited by examiner

*Primary Examiner* — Nannette Holloman
(74) *Attorney, Agent, or Firm* — Polsinelli PC

(57) ABSTRACT

The instant disclosure relates to methods and kits that improve the cosmetic properties of hair, especially hair treated with a chemical relaxer composition. The methods entail treating hair with a combination of different hair-treatment compositions. For example, hair (especially chemical relaxed hair) is treated with a hair-treatment composition comprising at least 0.5 wt. %, based on the total weight of the hair-treatment composition, of at least one non-polymeric mono, di, or tricarboxylic acid, and/or a salt thereof; one or more amines; and water. The hair is subsequently treated with an auxiliary composition, which includes one or more polyurethane latex polymers. Hair treated according to the disclosed methods, especially chemically relaxed hair, exhibits improved style-control and discipline, frizz control, smoothness, softness, and strength.

36 Claims, No Drawings

METHODS AND KITS FOR TREATING CHEMICALLY RELAXED HAIR

FIELD OF THE DISCLOSURE

The instant disclosure relates to methods and kits for treating hair, especially chemically relaxed hair. The methods and kits provide hair with a variety of benefits, such as improved manageability, long-lasting style and frizz control, strength, and smoothness.

BACKGROUND

Many chemical treatments are available for changing the appearance of hair. For example, chemical treatments for permanently straightening or curling the hair are common. In addition, hair may be lightened or bleached and oxidative dyes used to change the color of the hair. Chemical treatments are popular because their effects are long lasting and can be drastic. Nonetheless, the biggest drawback to chemical treatments is the strain and damage caused to hair. This is because chemical treatments permanently change the chemical and physical structure of the hair.

Chemical treatments can remove moisture from the surface of the hair cuticles resulting in the hair becoming brittle, dry, and more vulnerable to breakage.

Individuals seeking to change the shape of hair often turn to chemical procedures that use chemical relaxer compositions. Chemical relaxer compositions are often used on curly hair. The chemical relaxer compositions make hair easier to straighten by chemically "relaxing" the natural curls. The active agent is often a strong alkali, although some formulations are based on ammonium thioglycolate instead. Hair relaxer compositions are applied to hair at a salon by a professional or in the home by the individual consumer.

Hair fiber is a keratinous material, which is comprised of proteins (polypeptides). Many of the polypeptides in hair fibers are bonded together by disulfide bonds (—S—S—). A disulfide bond may be formed from the reaction of the two sulfhydryl groups (—SH), one on each of two cysteine residues, which results in the formation of a cystine residue. While there may be other types of bonds between the polypeptides in hair fibers, such as ionic salt bonds, the permanent curling and shape of the hair is essentially dependent on the disulfide bonds of cystine residues.

Chemical relaxing processes alter the aforementioned disulfide bonds between polypeptides in hair fibers to form lanthionine [$S(CH_2CHNH_2COOH)_2$]. Thus, the term "lanthionizing" is often used when referring to the relaxing or straightening of keratin fibers by hydroxide ions. Hair fibers may be relaxed or straightened by disrupting the disulfide bonds of the hair fibers with an alkaline agent or with a reducing agent. The chemical disruption of disulfide bonds with an alkaline agent is generally combined with mechanical straightening of the hair, such as combing, and straightening generally occurs due to changes in the relative positions of opposing polypeptide chains within the hair fiber. This reaction is generally terminated by rinsing and/or application of a neutralizing composition.

The reaction with the alkaline agent is normally initiated by hydroxide ions. Hair relaxing processes proceed via the release of the hydroxide ions, which penetrate the hair fiber and transform cystine residues to lanthionine residues. Chemical relaxer compositions often contain varying proportions of strong water-soluble bases, such as sodium hydroxide (NaOH), or include slightly-soluble metal hydroxides, such as calcium hydroxide ($Ca(OH)_2$), which can be converted in situ to soluble bases, such as guanidine hydroxide. Sodium hydroxide is extremely effective in straightening hair fibers but often causes a decrease in the strength of the hair fibers. Chemical relaxer composition often damage the hair to an extent and cause the hair to lose some of its desirable cosmetic properties such as shine, strength, smoothness, etc. Thus, mechanisms to reduce or prevent damage to hair and for improving the cosmetic properties of hair treated with chemical relaxer compositions are desired.

SUMMARY OF THE DISCLOSURE

The instant disclosure relates to methods and kits for treating hair, for example, for imparting desirable cosmetic properties to the hair, especially chemically relaxed hair. The disclosed methods and kits strengthen hair and compensate for damage to hair caused by chemical treatments including chemical relaxer treatments. Hair treated according to the disclosed methods exhibits improved style-control, strength, discipline, frizz control, smoothness, and softness. The methods typically include:

applying to the hair a hair-treatment composition comprising:
at least 0.5 wt. %, based on the total weight of the hair-treatment composition, of at least one non-polymeric mono, di, or tricarboxylic acid, and/or a salt thereof;
one or more amines selected from the group consisting of diamines, polyamines, alkylamines, alkanolamines, and/or a mixture thereof; and
water; and
applying to the hair an auxiliary composition comprising:
one or more polyurethane latex polymers.

The methods are particularly useful for treating chemically relaxed hair. Therefore, in some cases, the hair-treatment composition is applied to hair within 30 minutes from rinsing a chemical relaxer composition from the hair, for example, while the hair is still wet or damp. After application, the hair-treatment composition may be allowed to remain on the hair for a period of time, although allowing the hair-treatment composition to remain on the hair for an extended period of time is not necessary. After the hair-treatment composition is rinsed from the hair, the auxiliary composition is applied to the hair.

Typically, the auxiliary composition is applied to the hair immediately or shortly after the hair-treatment composition is rinsed from the hair (e.g., within about 30 minutes, while the hair is still wet or damp). The auxiliary composition may be applied to the hair independently or it may be combined or layered with another composition, such as a shampoo, a conditioner, or a conditioning shampoo (all-in-one shampoo/conditioner), and the combination is applied to the hair. After application, the auxiliary composition may be allowed to remain on the hair for a period of time, although allowing the auxiliary composition to remain on the hair for an extended period of time is not necessary. After rinsing the auxiliary composition from the hair, the hair may be dried and styled. For example, the hair may be dried with a blow drier and/or styled with a hot iron (e.g., a flat iron, a curling iron, etc.).

In some instances, the methods also include applying a conditioning composition to the hair. The conditioning composition may be applied to the hair and rinsed from the hair before the hair-treatment composition is applied to the hair. Alternatively, the conditioning composition may be applied to the hair after a hair-treatment composition has been applied and rinsed from the hair. In some cases, a conditioning composition and a hair-treatment composition are combined and applied to the hair together. In any event, the conditioning composition is typically applied to the hair and typically rinsed from the hair before an auxiliary composition is applied to the hair.

In some cases, the conditioning composition is layered on top of the hair-treatment composition (i.e, a hair-treatment composition is first applied to the hair and without rinsing the hair-treatment composition from the hair a conditioning composition is applied to the hair). Alternatively, in some cases, a hair-treatment composition is layered on top of a conditioning composition (i.e., a conditioning composition is first applied to the hair and without rinsing the conditioning composition from the hair a hair-treatment composition is applied to the hair).

After rinsing the hair-treatment composition and the conditioning composition from the hair, the auxiliary composition is applied to the hair. Typically, the auxiliary composition is applied to the hair immediately or shortly after rinsing the hair-treatment composition and the conditioning composition from the hair (e.g., within about 30 minutes, while the hair is still wet or damp). The auxiliary composition may be applied to the hair independently or it may be combined or layered with another composition, such as a shampoo, a conditioner, or a conditioning shampoo (all-in-one shampoo/conditioner), and the combination applied to the hair. After application, the auxiliary composition may be allowed to remain on the hair for a period of time, although allowing the auxiliary composition to remain on the hair for an extended period of time is not necessary. After rinsing the auxiliary composition from the hair, the hair may be dried and styled. For example, the hair may be dried with a blow drier and/or styled with a hot iron (e.g., a flat iron, a curling iron, etc.).

One or more of the various compositions of the methods (e.g., the hair-treatment compositions, the conditioning compositions, and the auxiliary compositions) may be included in a kit. Accordingly, the instant disclosure relates to kits comprising the compositions of the instant disclosure. The methods and kits are unique in their ability to provide hair with improved manageability, long-lasting style and frizz control, strength, and smoothness. Thus, the instant disclosure also relates to methods for improving the manageability of hair, for imparting lasting style and frizz control, for strengthening the hair, and for imparting smoothness and/or shine to the hair, etc.

DETAILED DESCRIPTION OF THE DISCLOSURE

The instant disclosure relates to methods for treating hair, in particular methods for treating chemically relaxed hair. The methods improve the cosmetic properties of hair, for example, the methods strengthen and/or compensate for the damage caused to hair during the chemical relaxing process and additionally provide improved style-control and discipline, frizz control, smoothness, softness, suppleness, and strength.

The methods entail treating hair with a combination of different compositions. For example, hair is treated with a hair-treatment composition comprising: at least 0.5 wt. % of at least one non-polymeric mono, di, and/or tricarboxylic acid, and/or a salt thereof; one or more amines; and water. The hair is also treated with an auxiliary composition comprising one or more polyurethane latex polymers.

More specifically, methods according to the disclosure include:
applying to the hair a hair-treatment composition comprising:
at least 0.5 wt. %, based on the total weight of the hair-treatment composition, of at least one non-polymeric mono, di, or tricarboxylic acid, and/or a salt thereof;
one or more amines selected from the group consisting of diamines, polyamines, alkylamines, alkanolamines, and/or a mixture thereof; and
water;
rinsing the hair-treatment composition from the hair;
applying to the hair an auxiliary composition comprising:
one or more polyurethane latex polymers; and
rinsing the auxiliary composition from the hair.

The hair-treatment composition is typically applied to the hair immediately or shortly after a chemical relaxer composition is rinsed from the hair, for example, while the hair is still wet or damp. Accordingly, a hair-treatment composition may be applied to the hair within about 30 minutes, 25 minutes, 20 minutes, 15 minutes, 10 minutes, or 5 minutes from rinsing a chemical relaxer composition from the hair.

The hair-treatment composition may be applied to the hair and allowed to remain on the hair for a period of time, although allowing the hair-treatment composition to remain on the hair for an extended period of time is not necessary. For instance, the hair-treatment composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes. After an optional period of time, the hair-treatment composition may be rinsed from the hair.

An auxiliary composition is typically applied to the hair after application of the hair-treatment composition, usually after the hair-treatment composition has been rinsed from the hair. The auxiliary composition may be applied to the hair independently or it may be combined or layered with another composition, such as a shampoo, a conditioner, or a conditioning shampoo (all-in-one shampoo/conditioner), and the combination applied to the hair. After rinsing the auxiliary composition (which is optionally combined with another composition such as a shampoo, conditioner, or conditioning shampoo) from the hair, the hair may be dried and styled. For example, the hair may be dried with a blow drier and styled with a hot iron (e.g., a flat iron, a curling iron, etc.).

The auxiliary composition (regardless of whether it is combined with another composition such as a shampoo, conditioner, or conditioning shampoo) may be allowed to remain on the hair for a period of time, although allowing the auxiliary composition to remain on the hair for an extended period of time is not necessary. For instance, the auxiliary composition (regardless of whether it is combined with another composition such as a shampoo, conditioner, or conditioning shampoo) may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes. After a period of time, the auxiliary composition may be rinsed from the hair. After the auxiliary composition is rinsed from the hair, the hair may be styled. For example, the hair may be blow dried and optionally further treated with a hot iron (e.g., a flat iron, a curling iron, etc.).

In some instances, the methods also include applying a conditioning composition to the hair. The conditioning composition includes one or more polyurethane latex polymers and may include at least one or more cationic surfactants and/or one or more fatty compounds. Exhaustive lists of useful cationic surfactants and fatty compounds are provided later, under the headings "Cationic Surfactants" and "Fatty Compounds." The conditioning composition may be applied to the hair and rinsed from the hair before the hair-treatment composition is applied to the hair. Alternatively, the conditioning composition may be applied to the hair after a hair-treatment composition has been applied and rinsed from the hair. In some cases, a conditioning composition and a hair-treatment composition are combined and applied to the hair together or layered onto the hair. In any event, the conditioning composition is typically applied to the hair and typically rinsed from the hair before an auxiliary composition is applied to the hair.

The conditioning composition may be allowed to remain on the hair for a period of time (a period of time that is independent of the period of time that the hair-treatment composition may be allowed to remain on the hair). For example, the conditioning composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes.

In some cases, the hair-treatment composition is rinsed from the hair and immediately or shortly thereafter, a conditioning composition is applied to the hair, for example while the hair is still wet or damp. For example, a conditioning composition may be applied to the hair within about 30 minutes, 25 minutes, 20 minutes, 15 minutes, 10 minutes, or 5 minutes from rinsing a hair-treatment composition from the hair.

In some cases, the hair-treatment composition is not rinsed from the hair prior to application of a conditioning composition. Rather, a conditioning composition is applied to the hair already covered with the hair-treatment compositions (the conditioner is layered onto the hair covered with a hair-treatment composition). The conditioning composition may be applied immediately or shortly after the hair-treatment composition is applied to the hair, for example, within about 30, 25, 20, 15, 10, 5, or 1 minute(s) from the time the hair-treatment composition is applied to the hair. After the conditioning composition has been applied to the hair, the hair may be rinsed to remove both the conditioning composition and the hair-treatment composition.

In some cases, the hair-treatment composition and the conditioning composition may be combined prior to application of either composition to the hair. For example, the hair-treatment composition and the conditioning composition may be mixed shortly before application to the hair, for example, within about within about 30, 25, 20, 15, 10, 5, or 1 minute(s) from when the mixture is applied to the hair. When combined with a conditioning composition, the hair-treatment composition may be used in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition:conditioning composition).

Finally, it is possible to apply a conditioning composition to the hair before applying the hair-treatment composition. The conditioning composition may be applied to the hair immediately or shortly after a chemical relaxer composition has been rinsed from the hair, for example, while the hair is still wet or damp. For example, a conditioning composition may be applied to the hair within about 30 minutes, 25 minutes, 20 minutes, 15 minutes, 10 minutes, or 5 minutes from rinsing a chemical relaxer composition from the hair.

In some cases, the conditioning composition is not rinsed from the hair prior to application of a hair-treatment composition. Rather, a hair-treatment composition is applied to the hair already covered with the conditioning composition (the conditioning composition is layered onto the hair covered with the conditioning composition). The hair-treatment composition may be applied immediately or shortly after the conditioning composition is applied to the hair, for example, within about 30, 25, 20, 15, 10, 5, or 1 minute(s) from the time the conditioning composition is applied to the hair. After the conditioning composition has been applied to the hair, the hair may be rinsed to remove the hair-treatment composition and the conditioning composition (remove the bulk of the hair-treatment composition and the conditioning composition). After rinsing the hair-treatment composition and the conditioning composition from the hair, an auxiliary composition may be applied to the hair, for example, while the hair is still wet or damp. For example, the auxiliary composition may be applied to the hair within about 30 minutes, 25 minutes, 20 minutes, 15 minutes, 10 minutes, or 5 minutes from rinsing a chemical relaxer composition from the hair.

As already indicated above, an auxiliary composition may be applied to the hair independently or it may be combined with another composition, such as a shampoo, a conditioner, or a conditioning shampoo (all-in-one shampoo/conditioner), and the combination applied to the hair. After rinsing the auxiliary composition (which is optionally combined with another composition such as a shampoo, conditioner, or conditioning shampoo) from the hair, the hair is typically dried and styled. For example, the hair may be dried with a blow drier and styled with a hot iron (e.g., a flat iron, a curling iron, etc.).

The auxiliary composition (regardless of whether it is combined with another composition such as a shampoo, conditioner, or conditioning shampoo) may be allowed to remain on the hair for a period of time, although allowing the auxiliary composition to remain on the hair for an extended period of time is not necessary. For instance, the auxiliary composition (regardless of whether it is combined with another composition such as a shampoo, conditioner, or conditioning shampoo) may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, or from about 10 seconds to about 5 minutes. After a period of time, the auxiliary composition may be rinsed from the hair. After the auxiliary composition is rinsed from the hair, the hair may be styled. For example, the hair may be blow dried and optionally further treated with a hot iron (e.g., a flat iron, a curling iron, etc.). In some instances, methods according to the disclosure include:

applying to the hair a hair-treatment composition comprising:
at least 0.5 wt. %, based on the total weight of the hair-treatment composition, of at least one non-polymeric mono, di, or tricarboxylic acid, and/or a salt thereof;
one or more amines selected from the group consisting of diamines, polyamines, alkylamines, alkanolamines, and/or a mixture thereof; and
water;
applying to the hair a conditioning composition comprising:
at least 0.5 wt. %, based on the total weight of the hair-treatment composition, of at least one non-polymeric mono, di, or tricarboxylic acid, and/or a salt thereof;
one or more cationic surfactants; and
one or more fatty compounds; and
applying to the hair an auxiliary composition comprising:
one or more polyurethane latex polymers.

The hair-treatment composition is typically applied to the hair immediately or shortly after a chemical relaxer composition is rinsed from the hair, for example, while the hair is still wet or damp. For example, a hair-treatment composition may be applied to the hair within about 30 minutes, 25 minutes, 20 minutes, 15 minutes, 10 minutes, or 5 minutes from rinsing a chemical relaxer composition from the hair.

The hair-treatment composition may be applied to the hair and allowed to remain on the hair for a period of time, although allowing the hair-treatment composition to remain on the hair for an extended period of time is not necessary. For instance, the hair-treatment composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes. After an optional period of time, the hair-treatment composition may be rinsed from the hair or it may be allowed to remain on the hair while a conditioning composition is applied to the hair.

The conditioning composition may be applied to the hair before or after the hair-treatment composition is rinsed from the hair. Moreover, the hair-treatment composition and the hair-conditioning composition can be combined prior to application to the hair.

In some cases, the hair-treatment composition is rinsed from the hair and immediately or shortly thereafter, a conditioning composition is applied to the hair, for example while the hair is still wet or damp. A conditioning composition may be applied to the hair within about 30 minutes, 25 minutes, 20 minutes, 15 minutes, 10 minutes, or 5 minutes from rinsing a hair-treatment composition from the hair.

After the hair-treatment composition is rinsed from the hair and the conditioning composition is applied to the hair, the conditioning composition may be allowed to remain on the hair for a period of time, although allowing the conditioning composition to remain on the hair for an extended period of time is not necessary. For example, the conditioning composition may be allowed to remain on the hair from about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes.

In some cases, the hair-treatment composition is not rinsed from the hair prior to application of a conditioning composition. Rather, a conditioning composition is applied to the hair already covered with the hair-treatment compositions (the conditioner is layered onto the hair covered with a hair-treatment composition). The conditioning composition may be applied immediately or shortly after the hair-treatment composition is applied to the hair, for example, within about 30, 25, 20, 15, 10, 5, or 1 minute(s) from the time the hair-treatment composition is applied to the hair.

The conditioning composition which is layered onto the hair may be allowed to remain on the hair for a period of time, a period of time that is subsequent to the optional period of time that the hair-treatment composition may have already been allowed to remain on the hair. Although a conditioning composition that is layered onto a hair-treatment composition may be allowed to remain on the hair for a period of time, allowing the conditioning composition to remain on the hair for an extended period of time is not necessary. For example, a hair-treatment composition may be allowed to first remain on the hair alone for a period of time (e.g., about 10 minutes), after which a conditioning composition is layered on top of the hair-treatment composition and the conditioning composition is then allowed to remain on the hair for a period of time (e.g., 10 minutes), while the underlying hair-treatment composition remains on the hair.

The hair conditioning composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes. After an optional period of time, the conditioning composition and the hair-treatment composition may be rinsed together from the hair.

In some cases, the hair-treatment composition and the conditioning composition may be combined prior to application of either composition to the hair. For example, the hair-treatment composition and the conditioning composition may be mixed shortly before application of the mixture to the hair, within about within about 30, 25, 20, 15, 10, 5, or 1 minute(s) from when the mixture is applied to the hair. When combined with a conditioning composition, the hair-treatment composition may be used in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition:conditioning composition). The combination of the hair-treatment composition and the conditioning composition may be allowed to remain on the hair for a period of time, although allowing the combination to remain on the hair for an extended period of time is not necessary.

The combination of hair-treatment composition and conditioning composition may be allowed to remain on the hair from about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes.

Finally, it is possible to apply a conditioning composition to the hair before applying the hair-treatment composition. The conditioning composition may be applied to the hair immediately or shortly after a chemical relaxer composition has been rinsed from the hair, for example, while the hair is still wet or damp. For example, a conditioning composition may be applied to the hair within about 30 minutes, 25 minutes, 20 minutes, 15 minutes, 10 minutes, or 5 minutes from rinsing a chemical relaxer composition from the hair.

The conditioning composition may be allowed to remain on the hair for a period of time although allowing the conditioning composition to remain on the hair for an extended period of time is not necessary. For example, the conditioning composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes.

In some cases, the conditioning composition is not rinsed from the hair prior to application of a hair-treatment composition. Rather, a hair-treatment composition is applied to the hair already covered with the conditioning composition (the hair-treatment composition is layered onto the conditioning composition already on the hair). The hair-treatment composition may be applied immediately or shortly after the conditioning composition is applied to the hair, for example, within about 30, 25, 20, 15, 10, 5, or 1 minute(s) from the time the conditioning composition is applied to the hair.

The hair-treatment composition which is layered onto the conditioning composition may be allowed to remain on the hair for a period of time, a period of time that is subsequent to the optional period of time that the conditioner composition may have already been allowed to remain on the hair. Although a hair-treatment composition that is layered onto a conditioning composition may be allowed to remain on the hair for a period of time, allowing the hair-treatment composition to remain on the hair for an extended period of time is not necessary. For example, a conditioner may be allowed to remain on the hair alone for a period of time (e.g., about 10 minutes), after which a hair-treatment composition is layered on top of the conditioning composition, and the hair-treatment composition is then allowed to remain on the hair for a period of time (e.g., 10 minutes), while the underlying conditioning composition remains on the hair.

The hair-treatment composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, from about 10 seconds to about 5 minutes, from about 1 minute to about 30 minutes, from about 1 minute to about 25 minutes, from about 1 minute to about 20 minutes, from about 1 minute to about 15 minutes, about 5 minutes to about 30 minutes, about 5 minutes to about 25 minutes, about 5 minutes to about 20 minutes, or about 5 minutes to about 15 minutes. After an optional period of time, the hair-treatment composition and the conditioning composition may be rinsed together from the hair.

After rinsing the hair-treatment composition and the conditioning composition from the hair, an auxiliary composition may be applied to the hair, for example, while the hair is still wet or damp. For example, the auxiliary composition may be applied to the hair within about 30 minutes, 25 minutes, 20 minutes, 15 minutes, 10 minutes, or 5 minutes from rinsing a chemical relaxer composition from the hair.

The auxiliary composition may be applied to the hair and allowed to remain on the hair for a period of time, although allowing the auxiliary composition to remain on the hair for an extended period of time is not necessary. For instance, the auxiliary composition may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, or from about 10 seconds to about 5 minutes. After a period of time, the auxiliary composition may be rinsed. After the auxiliary composition is rinsed from the hair, the hair may be styled. For example, the hair may be blow dried and optionally further treated with a hot iron (e.g., a flat iron, a curling iron, etc.).

The methods of the disclosure impart a variety of beneficial properties to the hair, especially chemically relaxed hair. Accordingly, the methods of the disclosure can be used in a variety of methods. Non-limiting examples include methods for:
  conditioning the hair;
  providing frizz control to the hair;
  improving ease of combability and detangling of hair;
  increasing the appearance of hair volume;
  protecting hair from damage;
  repairing damaged hair;
  strengthening hair;
  imparting softness to hair; and/or
  improving the hair shine and/or luster.

The various components and compositions used in the disclosed methods may be included in kits. For example, a kit may include at least one hair-treatment composition, and at least one auxiliary composition; wherein each composition is separately contained. In some cases, the kit may further include at least one separately contained conditioning composition. Furthermore, a kit may include any two of the following: a hair-treatment composition, a conditioning composition, and an auxiliary composition. In some cases, the kits may also include a shampooing or cleansing composition. Instructions, mixing components, brushes, gloves, measuring tools, etc., may also be included in the kits. A non-limiting exemplary kit may include:
  a hair-treatment composition comprising:
    at least 0.5 wt. % of at least one non-polymeric mono, di, or tricarboxylic acid, and/or a salt thereof, based on the total weight of the hair-treatment composition;

one or more amines selected from the group consisting of diamines, polyamines, alkylamines, alkanolamines, and a mixture thereof; and water;

a conditioning composition comprising:
one or more cationic surfactants; and
one or more fatty compounds; and an auxiliary composition comprising:
one or more polyurethane latex polymers;

wherein the hair-treatment composition, the conditioning composition, and the auxiliary composition are separately contained.

The various compositions (hair-treatment compositions, conditioning compositions, and auxiliary compositions) that are useful in the methods and kits of the disclosure are described in more detail in the following sections.

Hair-Treatment Compositions

The hair-treatment compositions of the instant disclosure typically include at least 0.5 wt. %, based on the total weight of the hair-treatment composition, of at least one non-polymeric mono, di, or tricarboxylic acid, and/or a salt thereof; one or more amines, for example, one or more amines selected from the group consisting of diamines, polyamines, alkylamines, alkanolamines, and/or a mixture thereof; and water.

A non-polymeric mono, di, and/or tricarboxylic acid is an organic compound having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of monocarboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair-treatment compositions include at least lactic acid and/or a salt thereof.

Non-limiting examples of dicarboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair-treatment compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair-treatment compositions include at least citric acid and/or a salt thereof.

In some cases, the hair-treatment compositions include at least one or more dicaboxylic acids, and/or a salt thereof, in particular, oxalic acid, malonic acid, malic acid, maleic acid, a salt thereof, or a mixture thereof. A particularly useful dicarboxylic acid is malonic acid and/or a salt thereof.

The total amount of the at least one non-polymeric mono, di, or tricarboxylic acid, and/or a salt thereof, is at least 0.5 wt. %, based on the total weight of the hair-treatment composition. In some cases, the total amount of the at least one non-polymeric mono, di, or tricarboxylic acid, and/or salt thereof, is at least 0.6, 0.7, 0.8, 0.9, or 1 wt. % up to about 15, 20, 25, or 30 wt. %. Furthermore, the total amount of the at least one non-polymeric mono, di, or tricarboxylic acid, and/or salt thereof, may be at least 0.5 wt. % to about 50 wt. %, at least 0.5 wt. % to about 40 wt. %, at least 0.5 wt. % to about 30 wt. %, at least 0.5 wt. % to about 20 wt. %, at least 0.5 wt. % to about 10 wt. %, at least 0.5 wt. % to about 5 wt. %, at least 0.8 wt. % to about 50 wt. %, at least 0.8 wt. % to about 40 wt. %, at least 0.8 wt. % to about 30 wt. %, about 0.8 to about 20 wt. %, about 0.8 to about 10 wt. %, about 0.8 wt. % to about 5 wt. %, about 1 wt. % to about 50 wt. %, about wt. % to about 40 wt. %, about 1 wt. % to about 30 wt. %, about 1 wt. % to about 20 wt. %, about 1 wt. % to about 10 wt. %, about 1 wt. % to about 5 wt. %, about 2 wt. % to about 50 wt. %, about 2 wt. % to about 40 wt. %, about 2 wt. % to about 30 wt. %, about 2 wt. % to about 20 wt. %, about 2 wt. % to about 10 wt. %, or about 2 wt. % to about 5 wt. %.

Non-limiting examples of the types of amines that may be used in the hair-treatment compositions are vast, but may include diamines, polyamines, alkylamines, alkanolamines, and mixtures thereof. The amines may be primary, secondary, tertiary amines, and mixtures thereof.

Non-limiting examples of diamines include ethylenediamine (1,2-diaminoethane), 1,3-diaminopropane (propane-1,3-diamine), putrescine (butane-1,4-diamine), cadaverine (pentane-1,5-diamine), hexamethylenediamine (hexane-1,6-diamine), 1,2-diaminopropane, diphenylethylenediamine, diaminocyclohexane, xylylenediamine (o-xylylenediamine, m-xylylenediamine, and p-xylylenediamine), phenylenediamine (o-phenylenediamine, m-phenylenediamine, p-phenylenediamine), 2,5-diaminotoluene, dimethyl-4-phenylenediamine, N,N'-di-2-butyl-1,4-phenylenediamine, 4,4'-diaminobiphenyl, 1,8-diaminonaphthalene, and mixtures thereof.

Polyamines have more than 2 amino groups and may be a polymer comprising multiple amino groups including homopolymers, copolymers, and terpolymers. For instance, the polyamine may be an alkoxylated polyamine having at least two amino groups and at least one degree of alkoxylation. The alkoxylation is provided by an alkylene oxide group such as, for example, ethylene oxide and/or propylene oxide. In some cases, the compositions do not include polymers having dimethylamino moieties, i.e., the compositions are free of essentially free of polyamines that are polymers having dimethylamino moieties.

Non-limiting examples of alkylamines and alkanolamines include compounds of formula (II):

  (II)

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$ alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

A more exhaustive list of amines that may be included in the hair-treatment compositions is provided later, under the heading "Amines."

The total amount of the one or more amines may vary, but in some cases, the total amount of the one or more amines is about 0.1 to about 50 wt. %, based on the total weight of the hair-treatment composition. In some cases, the total amount of the one or more amines is about 0.1 to about 50 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 3 to about 8 wt. %.

In some instances, the hair-treatment compositions may include one or more alkoxysilanes. Non-limiting examples include methyltrimethoxysilane, methyltriethoxysilane, glycidoxypropyltrimethoxysilane, vinyltrimethoxysilane methacryloxypropyl-trimethoxysilane, methacryloxypropyltrimethoxysilane, acryloxypropyltrimethoxysilane, vinyltrimethoxysilane, glycidoxypropyltriethoxysilane, glycidoxypropyltrimethoxysilane, aminopropyltriethoxysilane, aminopropyltrimethoxysilane, mercaptopropyl-trimethoxysilane, mercaptopropyltriethoxysilane, and a mixture thereof. Additional non-limiting examples include vinyltrimethoxysilane, vinyltriethoxysilane, vinyltripropoxysilane, aryltrimethoxysilane, aryltriethoxysilane, N-(3-acryloxy-2-hydroxypropyl)-3-aminopropyltriethoxysilane, N-(3-acryloxy-2-hydroxypropyl)-3-aminopropyltrimethoxysilane, N-(3-acryloxy-2-hydroxypropyl)-3-aminopropyltripropoxysilane, 3-acryloxypropylmethylbis(trimethoxy)silane, 3-acryloxypropyltrimethoxysilane, 3-acryloxypropyltriethoxysilane, 3-acryloxypropyltripropoxysilane, 3-(meth)acryloxypropyltrimethoxysilane, 3-(meth)acryloxypropyltriethoxysilane, 3-(meth)acryloxypropyltripropoxysilane, styrylethyltrimethoxysilane and a mixture thereof. In some instances, particularly useful alkoxysilanes include 3-mercaptopropyltriethoxysilane and/or 3-aminopropyltriethoxysilane. A more exhaustive list of alkoxysilanes that may be included in the hair-treatment compositions is provided later, under the heading "Alkoxysilanes."

The total amount of the one or more alkoxysilanes may vary but is typically about 0.1 to about 20 wt. %, based on the total weight of the hair-treatment composition. The total amount of the one or more alkoxysilanes may be about 0.1 to about 15 wt. %, about 0.1 to about 10 wt. %, about 0.1 to about 8 wt. %, about 0.1 to about 6 wt. %, about 0.5 to about 20 wt. %, about 0.5 to about 15 wt. %, about 0.5 to about 10 wt. %, about 0.5 to about 8 wt. %, about 0.5 to about 6 wt. %, about 1 to about 20 wt. %, about 1 to about 15 wt. %, about 1 to about 10 wt. %, about 1 to about 8 wt. %, or about 1 to about 6 wt. %.

One or more cationic polymers may optionally be included in the hair-treatment compositions. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the hair-treatment compositions include one or more polyquaternium polymers, for example, polyquaternium-6. A more exhaustive list of cationic polymers that may be included in the hair-treatment compositions is provided later, under the heading "Cationic Polymers."

The total amount of the one or more cationic polymers may vary but is typically about 0.01 to about 10 wt. %, based on the total amount of the hair-treatment composition. The total amount of the one or more cationic polymers may be about 0.01 to about 8 wt. %, about 0.01 to about 6 wt. %, about 0.01 to about 4 wt. %, about 0.05 to about 10 wt. %, about 0.05 to about 8 wt. %, about 0.05 to about 6 wt. %, about 0.05 to about 4 wt. %, about 0.1 to about 10 wt. %, about 0.1 to about 8 wt. %, about 0.1 to about 6 wt. %, or about 0.1 to about 4 wt. %.

In one embodiment, the hair-treatment compositions of the instant disclosure may include:
  at least 0.5 wt. %, about 1 to about 15 wt. or about 5 to about 15 of at least one non-polymeric mono, di, or tricarboxylic acid, and/or a salt thereof;
  about 0.1 to about 20 wt. %, about 0.1 to about 15 wt. %, or about 1 to about 10 wt. % of one or more amines selected from the group consisting of diamines, polyamines, alkylamines, alkanolamines, and a mixture thereof;
  about 0.1 to about 20 wt. %, about 0.1 to about 15 wt. %, or about 0.1 to about 10 wt. % of one or more alkoxysilanes;
  about 0.01 to about 10 wt. %, about 0.01 to about 8 wt. %, or about 0.1 to about 6 wt. % of one or more cationic polymers; and
  water.

In one embodiment, the hair-treatment compositions of the instant case include:
  at least 0.5 to about 20 wt. %, about 1 to about 15 wt. %, or about 5 to about 15 wt. % of at least one non-polymeric mono, di, or tricarboxylic acid and/or a salt thereof, for example, one or more dicarboxylic acids and/or a salt thereof, selected from the group consisting of oxalic acid, malonic acid, malic acid, maleic acid, a salt thereof, or a mixture thereof (such as malonic acid and/or a salt thereof);
  about 1 to about 20 wt. %, about 1 to about 15 wt. %, or about 1 to about 10 wt. % of one or more alkanolamines, for example, one or more alkanoloamines, for example, one or more alkonolamines selected from the group consisting of monoethanolamine, 2-aminopropan-1-ol and 1-aminopropan-2-ol, 1,2,3-triaminopropane, 1,3-diaminopropan-2-ol, 1,2-diamino-propan-3-ol, 1-aminopropanediol, 2-aminopropanediol, glucosamine, isomaltine, and a mixture thereof;
  about 0.1 to about 20 wt. %, about 0.1 to about 15 wt. %, or about 0.1 to about 10 wt. % of one or more alkoxysilanes, for example, one or more alkoxysilanes selected from the group consisting of 3-mercaptopropyltriethoxysilane, 3-aminopropyltriethoxysilane, and a mixture thereof; and about 0.01 to about 10 wt. %, about 0.01 to about 8 wt. %, or about 0.1 to about 8 wt. % of one or more cationic polymers.

In yet another embodiment, the hair-treatment compositions may include:

at least 0.5 to about 20 wt. %, about 1 to about 15 wt. %, or about 2 to about 15 wt. % of malonic acid, and/or a salt thereof;

about 1 to about 20 wt. %, about 1 to about 15 wt. %, or about 1 to about 10 wt. % of monoethanolamine;

about 0.1 to about 20 wt. %, about 0.1 to about 15 wt. %, or about 0.1 to about 10 wt. % of 3-mercaptopropyltriethoxysilane and/or 3-aminopropyltriethoxysilane; and about 0.01 to about 10 wt. %, about 0.01 to about 8 wt. %, or about 0.1 to about 6 wt. % of one or more cationic polymers selected from polyquaterniums, in particular, polyquaternium-6.

Conditioning Compositions

The conditioning compositions typically include one or more cationic surfactants. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof. A more exhaustive list of cationic surfactants that may be included in the conditioning compositions is provided later, under the heading "Cationic Surfactants."

The total amount of the one or more cationic surfactants is typically about 0.1 to about 20 wt. %, based on the total weight of the conditioner composition. Additionally, the total amount of the one or more cationic surfactants may be about 0.1 to about 15 wt. %, about 0.1 to about 10 wt. %, about 0.1 to about 5 wt. %, about 0.1 to about 3 wt. %, about 0.5 to about 15 wt. %, about 0.5 to about 10 wt. %, about 0.5 to about 5 wt. %, about 0.5 to about 3 wt. %, about 1 wt. % to about 15 wt. %, about 1 wt. % to about 10 wt. %, or about 1 wt. % to about 5 wt. %.

One or more fatty compounds can be included in the hair-treatment compositions. Non-limiting examples of fatty compounds include oils, mineral oil, fatty alcohols, fatty acids, alkyl ethers of fatty alcohols, fatty acid esters of fatty alcohols, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which are incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyl-dodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and mixtures of all of the foregoing compounds.

Non-limiting polyglycerol esters of fatty acids include those of the following formula:

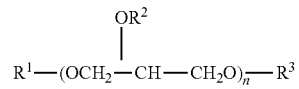

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of a nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substitued fatty acids, and a mixture thereof. Nonlimiting examples of fatty acid derivatives inlcude ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, ethylene glycol distearate (glycol distearate), propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. A more exhaustive list of fatty compounds that may be included in the hair-treatment compositions is provided later, under the heading "Fatty Compounds."

The total amount of the one or more fatty compounds may be about 0.1 to about 40 wt. %, based on the total weight of the conditioning composition. In some cases, the total amount of the one or more fatty compounds may be about 0.1 to about 30 wt. %, about 0.1 to about 20 wt. %, about 0.1 to about 20 wt. %, about 0.1 to about 10 wt. %, about 1 wt. % to about 40 wt. %, about 1 wt. % to about 30 wt. %, about 1 wt. % to about 20 wt. %, or about 1 wt. % to about 10 wt. %.

The conditioning compositions may optionally include at least one non-polymeric mono, di, or tricarboxylic acid, and/or a salt thereof, typically in an amount of at least 0.5 wt. %, based on the total weight of the conditioning composition. In some cases, it is desirable to include at least one non-polymeric mono, di, or tri-carboxylic acid, and/or salt thereof, but in other cases, inclusion of at least one non-polymeric mono, di, or tricarboxylic acid, and/or salt thereof, is not necessary.

Non-limiting examples of mono-carboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair-treatment compositions include at least lactic acid and/or a salt thereof.

Non-limiting examples of dicarboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the conditioning compositions include oxalic acid, malonic acid, malic acid, maleic acid, a salt thereof, a salt thereof, or a mixture thereof. In some cases, the conditioning composition include maleic acid, malonic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair-treatment compositions include at least citric acid and/or a salt thereof.

The total amount of the at least one non-polymeric mono, di, or tricarboxylic acid, and/or a salt thereof, is at least 0.5 wt. %, based on the total weight of the conditioning composition. In some cases, the total amount of the at least one non-polymeric mono, di, or tricarboxylic acid, and/or salt thereof, is at least 0.6, 0.7, 0.8, 0.9, or 1 wt. % up to about 15, 20, 25, or 30 wt. %. Furthermore, the total amount of the at least one non-polymeric mono, di, or tricarboxylic acid, and/or salt thereof, may be at least 0.5 wt. % to about 50 wt. %, at least 0.5 wt. % to about 40 wt. %, at least 0.5 wt. % to about 30 wt. %, at least 0.5 wt. % to about 20 wt. %, at least 0.5 wt. % to about 10 wt. %, at least 0.5 wt. % to about 5 wt. %, at least 0.8 wt. % to about 50 wt. %, at least 0.8 wt. % to about 40 wt. %, at least 0.8 wt. % to about 30 wt. %, about 0.8 to about 20 wt. %, about 0.8 to about 10 wt. %, about 0.8 wt. % to about 5 wt. %, about 1 wt. % to about 50 wt. %, about wt. % to about 40 wt. %, about 1 wt. % to about 30 wt. %, about 1 wt. % to about 20 wt. %, about 1 wt. % to about 10 wt. %, about 1 wt. % to about 5 wt. %, about 2 wt. % to about 50 wt. %, about 2 wt. % to about 40 wt. %, about 2 wt. % to about 30 wt. %, about 2 wt. % to about 20 wt. %, about 2 wt. % to about 10 wt. %, or about 2 wt. % to about 5 wt. %.

In one embodiment the conditioning compositions may include:

- optionally, at least 0.5 to about 10 wt. %, about 1 to about 8 wt. %, or about 1 to about 5 wt. % of at least one non-polymeric mono, di, or tricarboxylic acid, and/or a salt thereof, preferably citric acid, lactic acid, maleic acid, malic acid, malonic acid, a salt thereof, and a mixture thereof, more preferably citric acid and/or lactic acid, and/or a salt thereof;
- about 0.1 to about 20 wt. %, about 0.1 to about 10 wt. %, or, about 0.1 to about 5 wt. % of one or more cationic surfactants;
- about 0.01 to about 20 wt. %, about 0.1 to about 20 wt. %, or about 1 to about 10 wt. % of one or more fatty compounds;
- about 0.01 to about 20 wt. %, about 0.01 to about 10 wt. %, or about 0.01 to about 5 wt. % of one or more water-soluble solvents; and
- water.

Auxiliary Compositions

The auxiliary compositions typically include one or more polyurethane latex polymers. The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly wellsuited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the auxiliary composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

In some cases, the auxiliary compositions may include one or more silicone-organic polymer hybrid compound. Silicone-organic polymer hybrid compounds include silicone polyvinyl acetate compounds. The silicone-organic polymer hybrid compounds may also be chosen from a cross-linked anionic copolymer comprised of organic polymer blocks and silicone blocks, resulting in a multiblock polymer structure. The silicone-organic polymer hybrid compounds may be cross-linked anionic copolymers comprising at least one cross-linked polysiloxane structural unit. Examples of these polymers are described in PCT publication WO2011069786, which is incorporated herein by reference in its entirety.

In some cases, a particularly useful silicone-organic polymer hybrid compound is the compound having the INCI name of crotonic acid/vinyl C8-12 isoalkyl esters/VA/bis-vinyldimethicone crosspolymer, which is a copolymer of crotonic acid, vinyl C8-12 isoalkyl esters and vinyl acetate crosslinked with bis-vinyldimethicone. This compound is commercially available from the company Wacker Chemie AG under the tradename WACKER BELSI P1101 (may also be known under the tradename Wacker BELSIL P101). Crotonic acid/vinyl C8-12 isoalkyl esters/VA/bis-vinyldimethicone crosspolymer is also known by the technical name of crotonic acid/vinyl C8-12 isoalkyl esters/VA/divinyldimethicone crosspolymer. A more exhaustive list of silicone-organic polymer hybrid compounds that may be included in the hair-treatment compositions is provided later, under the heading "Silicone-Organic Polymer Hybrid Compounds."

The total amount of the one or more silicone-organic polymer hybrid compounds may vary but is typically about 0.01 to about 10 wt. %, based on the total weight of the auxiliary composition. The total amount of the one or more silicone-organic polymer hybrid compounds may be about 0.01 to about 8 wt. %, about 0.01 to about 6 wt. %, about 0.01 to about 5 wt. %, about 0.05 to about 10 wt. %, about 0.05 to about 8 wt. %, about 0.05 to about 6 wt. %, or about 0.05 to about 5 wt. %.

The auxiliary compositions may also optionally include one or more silicones that are different than the one or more silicone-organic polymer hybrid compounds. Many silicones that are different than the one or more silicone-organic polymer hybrid compounds are well known. Non-limiting examples of silicones include polyorganosiloxanes, polyalkylsiloxanes, polyarylsiloxanes, polyalkarylsiloxanes, polyestersiloxanes, and a mixture thereof. In particular, suitable non-limiting examples of silicones include dimethicone, cyclomethicone, amodimethicone, trimethyl silyl amodimethicone, phenyl trimethicone, trimethyl siloxy silicate, and mixtures thereof. In some cases, the hair-treatment compositions may include dimethicone, lauryl PEG/PPG-18/18 methicone, dimethiconol, amodimethicone, cyclomethicone, phenyl trimethicone, and a mixture thereof. A more exhaustive list of silicones that may be included in the hair-treatment compositions is provided later, under the heading "Silicones."

The total amount of the one or more silicones (silicones other that are different than the one or more silicone-organic polymer hybrid compounds) may vary but is typically about 0.01 to about 40 wt. %, based on the total weight of the auxiliary composition. In some cases, the total amount of the one or more silicones is about 0.01 to about 30 wt. %, about 0.1 to about 40 wt. %, about 0.1 to about 30 wt. %, about 0.1 to about 25 wt. %, about 1 to about 40 wt. %, about 1 to about 30 wt. %, about 1 to about 25 wt. %, about 5 to about 40 wt. %, about 5 to about 30 wt. %, or about 5 to about 25 wt. %.

The auxiliary compositions, in some cases, may contain one or more thickeners (also referred to as thickening agents or viscosity modifying agents). Classes of such agents include, but are not limited to, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition. In some cases, associative thickening polymers may be useful in anionic surfactant-free hair-treatment compositions, in particular, anionic surfactant free conditioning shampoos. For example, the anionic surfactant-free conditioning shampoos may include one or more anionic associative polymers. A more exhaustive list of thickening polymers that may be included in the auxiliary compositions is provided later, under the heading "Thickening Polymers."

The total amount of the one or more thickening agents may vary, but in some cases is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about wt. %, about 0.5 to about 5 wt. %, about 1 to about 10 wt. %, about 1 to about 8 wt. %, about 1 to about 6 wt. %, or about 1 to about 5 wt. %, based on the total weight of the auxiliary composition.

Additionally, one or more cationic polymers may be included in the hair-treatment compositions. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the hair-treatment compositions include one or more polyquaternium polymers. A more exhaustive list of cationic polymers that may be included in the hair-treatment compositions is provided later, under the heading "Cationic Polymers."

The total amount of the one or more cationic polymers may vary but is typically about 0.01 to about 10 wt. %, based on the total amount of the auxiliary composition. The total amount of the one or more cationic polymers may be about 0.01 to about 8 wt. %, about 0.01 to about 6 wt. %, about 0.01 to about 4 wt. %, about 0.05 to about 10 wt. %, about 0.05 to about 8 wt. %, about 0.05 to about 6 wt. %, about 0.05 to about 4 wt. %, about 0.1 to about 10 wt. %, about 0.1 to about 8 wt. %, about 0.1 to about 6 wt. %, or about 0.1 to about 4 wt. %.

One or more film-forming polymers other than the one or more polyurethane latex polymers may also be included in the hair-treatment compositions. For instance, non-limiting examples of film-forming polymers include vinyl polymers, polyesters, polyamides, polyureas, and a mixture thereof. The one or more film-forming polymers may be polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, maleic, fumaric and/or itaconic acid or anhydride polymers, polyamidoamines, and a mixture thereof.

The one or more film-forming polymers may be copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl(meth)acrylate and/or isobutyl (meth)acrylate/$C_1$-$C_4$ alkyl(meth)acrylate copolymers; (meth)acrylic acid/ethyl acrylate/methyl methacrylate terpolymers and tetrapolymers; methyl methacrylate/butyl or ethyl acrylate/hydroxyethyl or 2-hydroxypropyl acrylate or methacrylate/(meth)acrylic acid tetrapolymers; copolymers of acrylic acid and of $C_1$-$C_4$ alkyl methacrylate; terpolymers of vinylpyrrolidone, of acrylic acid and of $C_{1-20}$ alkyl methacrylate; amphoteric copolymers; vinyl esters of branched acids; vinyl esters of benzoic acid; copolymers of (meth)acrylic acid and of at least one olefinic monomer; copolymers of vinyl monoacid and/or allylic monoacid; and a mixture thereof. In some cases, the one or more film-forming polymers include VP/dimethylaminoethylmethacrlate copolymer. A more exhaustive list of film-forming polymers that may be included in the hair-treatment compositions is provided later, under the heading "Film-Forming Polymers."

The total amount of the one or more film-forming polymers (other than the one or more latex polymers) may vary but is typically about 0.01 to about 10 wt. %, based on the total weight of the auxiliary composition. The total amount of the one or more film-forming polymers (other than the one or more latex polymers) may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, or about 0.1 to about 5 wt. %.

In one embodiment, the auxiliary compositions of the instant case include:
- about 0.01 to about 10 wt. %, about 0.1 to about 10 wt. %, or about 1 to about 5 wt. % of polyurethane-34;
- about 0.01 to about 10 wt. %, about 0.01 to about 8 wt. %, or about 0.01 to about 5 wt. % of crotonic acid/vinyl C8-12 isoalkyl esters/VA/bis-vinyldimethicone crosspolymer;
- about 1 to about 50 wt. %, about 1 to about 40 wt. %, or about 5 to about 30 wt. % of one or more silicones selected from the group consisting of dimethicone, dimethiconol, phenyl trimethicone, cyclomethicone, amodimethicone, trimethyl silyl amodimethicone, trimethyl siloxy silicate, and mixtures thereof;
- about 0.01 to about 10 wt. %, about 0.01 to about 6 wt. %, or about 0.1 to about 5 wt. % of one or more thickening agents selected from the group consisting of hydroxypropyl guar gum, hydroxyethyl cellulose, starch-based polymers, and a mixture thereof;
- about 0.01 to about 10 wt. % of one or more cationic polymers comprising a polquaternium; and
- about 50 to about 95 wt. % of water.

More exhaustive but non-limiting lists of components useful in the hair-treatment compositions, including the conditioning compositions, the auxiliary compositions, etc., disclosed herein are provided below.

Amines

Diamines

Non-limiting examples of diamines that may be useful may be primary amines and secondary amines. The diamine can include both primary and secondary amine groups. Optional diamines may include at least one ethylene oxide group. For example, between 1 and 4 ethylene oxide groups can be present in the diamine. The diamine may optionally include propylene oxide groups. For example, between 1 and 4 propylene oxide groups can be present in the diamine. Non-limiting examples of diamines include 4,9-dioxadodecane-diamine; 4,7,10-trioxa-1,13-tridecanediamine; ethylenediamino; polyoxypropylene diamine; polyethylene glycol diamine; triethylene glycol diamine (2OE); n-(2-hydroxyethyl)-ethylenediamine; 1,3-diaminopropane; 1,7-diaminoheptane; 1,4-diaminobutane; 1,2-diaminopropane; 1,6-diaminohexane; 1,11-diamino-3,6,9-trioxaundecane; 1,5-diaminopentane; polyoxyethylene diamine; 2,2-dimethyl-1,3-propanediamine; 2,2-bis(aminoethoxy)propane; 4,7,10-trioxa-1,13-tridecanediamine; 1,3-diaminopentane; 4,7,10-trioxa-1,13; 1,5-diamino-2-methylpentane; (3s,4s)-(−)-3,4-hexanediamine dihydrochloride; 1,9-diaminononane, and mixtures thereof.

In some cases, diamines may be selected from the group consisting of 4,9-dioxadodecane-diamine, 4,7,10-trioxa-1,13-tridecanediamine, ethylenediamino, polyoxypropylene diamine, polyethylene glycol diamine, triethylene glycol diamine (2OE); n-(2-hydroxyethyl)-ethylenediamine; 1,3-diaminopropane, 1,7-diaminoheptane, 1,4-diaminobutane, 1,2-diaminopropane, 1,6-diaminohexane, 1,11-diamino-3,6,9-trioxaundecane, 1,5-diaminopentane, polyoxyethylene diamine, 2,2-dimethyl-1,3-propanediamine, 2,2-bis(aminoethoxy)propane, 4,7,10-trioxa-1,13-tridecanediamine, 1,3-diaminopentane, 4,7,10-trioxa-1,13; 1,5-diamino-2-methylpentane, (3s,4s)-(−)-3,4-hexanediamine dihydrochloride, 1,9-diaminononane, and mixtures thereof.

Polyamines

Polyamines have more than two amino groups. In some cases, the composition of the instant disclosure may include one or more polyamines, but in some cases, the compositions are free or essentially free of polyamines. The polyamine may be, for example, aminated polysaccharides comprising multiple amino groups, such as, for example, hydrolysates of aminated polysaccharides.

The polyamine may also be a polymer comprising multiple amino groups including homopolymers, copolymers, and terpolymers.

In some cases, polyamines are chosen from polyethyleneimines. Polyethyleneimines may optionally be substituted. Non-limiting examples of polyethyleneimines which may be used include LUPASOL products commercially available from BASF. Suitable examples of LUPASOL polyethyleneimines include LUPASOL PS, LUPASOL PL, LUPASOL PR8515, LUPASOL G20, LUPASOL G35 as well as LUPASOL SC Polythyleneimine Reaction Products (such as LUPASOL SC-61B, LUPASOL SC-62J, and LUPASOL SC-86X). Other non-limiting examples of poly-ethyleneimines which may be used in the composition according to the present invention are the EPOMIN products commercially available from Aceto. Suitable examples of EPOMIN polyethyleneimines include EPOMIN SP-006, EPOMIN SP-012, EPOMIN SP-018, and EPOMIN P-1000. Suitable polyamines s also be chosen from polyvinylamines. Examples thereof include LUPAMINES 9095, 9030, 9010, 5095, 1595 from BASF.

The polyamine compounds can also be substituted. An example of such a compound is PEG-15 Cocopolyamine from Cognis.

In some cases, the polyamine is chosen from proteins and protein derivatives. Non-limiting examples of suitable proteins and protein derivatives f include those listed at pages 1701 to 1703 of the C.T.F.A. International Cosmetic Ingredient Dictionary and Handbook, 8$^{th}$ edition, vol. 2, (2000), which is incorporated herein by reference in its entirety. In some cases, the at least one polyamine is chosen from wheat protein, soy protein, oat protein, collagen, and keratin protein.

The polyamine may be an alkoxylated polyamine. The alkoxylated polyamines may be chosen from amine compounds having at least two amino groups and at least one degree of alkoxylation. The alkoxylation is provided by an alkylene oxide group which may be chosen from ethylene oxide and propylene oxide. Non-limiting examples of suitable alkoxylated polyamines include compounds corresponding to the following formula:

$$NH_2R(R'CHCH_2O)_x(R'CHCH_2O)_y(R'CHCH_2O)_z—RNH_2$$

wherein R represents a —CH2-, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted; x, y, and z independently of one another, represent numbers of from 0 to about 100; R' represents hydrogen, or an alkyl group, preferably a methyl group; and The sum of x+y+z is at least 1. In some cases, R is a linear or branched, acyclic alkyl or alkenyl group or an alkyl phenyl group; x, y, and z independently of one another, preferably represent numbers ranging from 2 to 100.

Non-limiting examples of the alkoxylated polyamines include, for example, tetradecyloxypropyl-1,3-diaminopropane; a $C_{12-14}$ alkyl oxypropyl-1,3-diaminopropane; a $C_{12-15}$ alkyloxypropyl amine and other similar materials that are commercially available from Tomah under the tradename of TOMAH DA-17. Other examples of alkoxylated polyamines are diamine compounds belonging to the Jeffamine series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting examples of suitable alkoxylated polyamines in the diamine form include compounds corresponding to the following formula:

$$NH_2(CH_2)_xOCH_2CH_2O(CH_2)_xNH_2$$

wherein x is 2 or 3.

Examples of alkoxylated polyamines are diamine compounds belonging to the JEFFAMINE series available from Huntsman Corporation, Salt Lake City, Utah, such as JEFFAMINE EDR148, and JEFFAMINE EDR176.

Additional non-limiting examples of alkoxylated polyamines in the triamine form include compounds corresponding to the following formula:

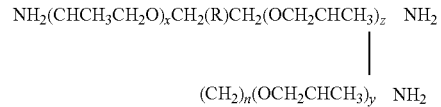

wherein R is hydrogen, —CH$_2$ or —C$_2$H$_5$, n=0 or 1, and x, y, and z independently of one another, represent numbers of from 0 to 100 and the sum of x+y+z is at least 1.

Examples of alkoxylated polyamines are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

Alkylamines and Alkanolamines

The one or more alkylamines and/or one or more alkanolamines that may be included in the compositions include compounds of formula (II):

$$NR_3R_4R_5 \qquad (II)$$

wherein R$_3$, R$_4$ and R$_5$ are independently H, C$_1$-C$_{40}$ alkyl, C$_1$-C$_{40}$ monohydroxyalkyl or C$_2$-C$_{40}$ polyhydroxyalkyl, provided that at least one of R$_3$, R$_4$ and R$_5$ is an alkyl or mono or polyhydroxyalkyl. In some cases, R$_3$, R$_4$ and R$_5$ are independently H, C$_1$-C$_2$ alkyl, C$_1$-C$_{20}$ monohydroxyalkyl or C$_2$-C$_{20}$ polyhydroxyalkyl, provided that at least one of R$_3$, R$_4$ and R$_5$ is an alkyl or mono or polyhydroxyalkyl. Finally, R$_3$, R$_4$ and R$_5$ may independently be H, C$_1$-C$_{10}$ alkyl, C$_1$-C$_{10}$ monohydroxyalkyl or C$_2$-C$_{10}$ polyhydroxyalkyl, provided that at least one of R$_3$, R$_4$ and R$_5$ is an alkyl or mono or polyhydroxyalkyl.

Non-limiting examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

$$RN(R')_2$$

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

In some cases, alkylamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of alkyl monoamines include amidoamine compounds corresponding to the following formula and their salts:

$$RCONHR'N(R'')_2$$

wherein: R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R'' is H or a hydrocarbon radical containing less than 6 carbon atoms. In addition, R'' is linear or branched, acyclic or cyclic, saturated or unsaturated, substituted or unsubstituted. Typically, R'' is a linear or branched, acyclic alkyl or alkenyl group. In some cases, R'' is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

Additional Amines

Additional amines that may be useful include alkoxylated monoamines. The alkoxylated monoamines are compounds having an amino group and at least one degree of alkoxylation. The alkoxylation is provided by an alkylene oxide group which is often chosen from ethylene oxide and propylene oxide.

Non-limiting examples of suitable alkoxylated monoamines include compounds corresponding to the following formula:

$$RN[(R'CHCH_2O)_xH][(R'CHCH_2O)_yH]$$

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 provided that the sum of x+y is >0; the groups R', which may be identical or different, represent hydrogen, or an alkyl group such as a methyl group. Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Non-limiting examples of alkoxylated monoamines include PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding the following formula:

$$RNR''[(R'CHCH_2O)_xH]$$

wherein R is a hydrocarbon radical containing at least 6 carbon atoms. R can be linear or branched, acyclic or cyclic, saturated or unsaturated, aliphatic or aromatic, substituted or unsubstituted; x represents a number of from 1 to 100; R' represents hydrogen, or an alkyl group such as in particular a methyl group; and R'' is a hydrogen or a hydrocarbon radical. Typically, R is a linear or branched, acyclic alkyl or alkenyl group or an alkyl phenyl group; x is typically a number from 1 to 30. When R'' is a hydrocarbon radical group, this group may be linear or branched, saturated or unsaturated, substituted or unsubstituted. The hydrocarbon radical represented by R'' may also contain an alkoxylated moiety (as defined by $[(R'CHCH_2O)_yH]$), and/or heteroatoms such as nitrogen. When R'' contains at least one alkoxylated moiety, the total number of alkoxylation in the formula may range from 1 to 120. Examples of alkoxylated monoamines include PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to the following formula:

$$R(R'CHCH_2O)_x(R'CHCH_2O)_yNH_y$$

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 with the proviso that the sum of x+y is >0; the groups R', which may be identical or different, represent hydrogen, or an alkyl group such as in particular a methyl group. Typically, R is a linear or branched, acyclic alkyl or alkenyl group or an alkyl phenyl group; x and y, independently of one another, are each typically a number from 0 to 30. Examples of alkoxylated monoamines include polyetheramines containing a monoamine group. These polyetheramines are commercially available from Hunstman under the tradename JEFFAMINE (M series such as M-600, M-1000, M-2005 and M-2070) and SURFONAMINE series (B-60, B-100, B-200, L-100, L-200, L-207, L-300).

Alkoxysilanes

The one or more alkoxysilanes often include at least one solubilizing functional group. As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents. Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In some cases, the one or more alkoxysilanes comprising at least one solubilizing functional group may comprise two or three alkoxy groups. For example, the alkoxy functional groups may be chosen from methoxy and ethoxy functional groups.

In some cases, the one or more alkoxysilanes comprising at least one solubilizing functional group may be selected from compounds of the following formula:

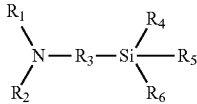

wherein, $R_4$ is chosen from halogen atoms, OR' groups, and $R_{11}$ groups;

$R_5$ is chosen from halogen atoms, OR'' groups, and $R_{12}$ groups;

$R_6$ is chosen from halogen atoms, OR''' groups, and $R_{13}$ groups;

$R_1$, $R_2$, $R_3$, R', R'', R''', $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R'', and R''' may also be chosen from hydrogen; provided that at least two groups $R_4$, $R_5$, and $R_6$ are different from $R_{11}$, $R_{12}$, and $R_{13}$, and at least two groups R', R'', and R''' are not hydrogen.

The one or more alkoxysilanes comprising at least one solubilizing functional group may also be one or more compounds chosen from compounds of the following formula:

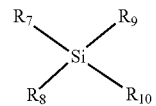

wherein $R_9$ is chosen from halogen atoms and OR'$_9$ groups;

$R_{10}$ is chosen from halogen atoms and OR'$_{10}$ groups;

R'$_9$ and R'$_{10}$, which may be identical or different, are chosen from hydrogen, and linear and branched, saturated and unsaturated $C_1$-$C_{14}$ hydrocarbon groups $R_7$ is a non hydrolyzable functional group providing a cosmetic effect; and $R_5$ is a non hydrolyzable functional group bearing at least one function chosen from amines, carboxylic acids and salts thereof, sulfonic acids and salts thereof, polyols such as glycol, polyethers such as polyalkylene ether, and phosphoric acids and salts thereof; and provided that at least one of $R_9$ and $R_{10}$ is not a halogen.

In some cases, the one or more alkoxysilanes comprising at least one solubilizing functional group may be chosen from compounds of the following formula:

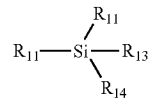

wherein $R_{12}$ is chosen from halogen atoms, OR'$_{12}$ groups, and $R_O$ groups;

$R_{13}$ is chosen from halogen atoms, OR'$_{13}$ groups, and R'$_O$ groups;

$R_{14}$ is chosen from halogen atoms, OR'$_{14}$ groups, and R''$_O$ groups;

$R_{11}$ is chosen from groups bearing at least one function chosen from carboxylic acids and salts thereof, sulfonic acids and salts thereof, and polyalkylethers;

Ro, R'o, R''o, R'$_{12}$, R'$_{13}$, and R'$_{14}$, which may be identical or different, are chosen from linear and branched, saturated and unsaturated, C1-$C_{14}$ hydrocarbon groups optionally bearing at least one additional chemical functional group chosen from carboxylic acids and salts thereof, sulfonic acids and salts thereof, and polyalkylether functions, and wherein R'$_{12}$, R'$_{13}$, and $R_{14}$ may also be chosen from hydrogen; provided that at least two groups from $R_{12}$, $R_{13}$ and $R_{14}$ are different from $R_O$, R'$_O$, and R''$_O$ groups; and provided further that at least two of the groups R'$_{12}$, R'$_{13}$, and R'$_{14}$ are not hydrogen.

According to another embodiment, the one or more alkoxysilanes comprising at least one solubilizing functional group may be chosen from compounds of the following formula:

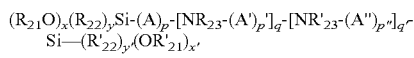

wherein $R_{21}$, $R_{22}$, R'$_{21}$, and R'$_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x is an integer ranging from 1 to 3;

y is 3-x;

x' is an integer ranging from 1 to 3;

y' is 3-x', p, p', p", q, and q' can each be 0 or 1, wherein at least one of q or q' is not equal to zero;

A, A', and A", which may be identical or different, are chosen from linear and branched $C_1$-$C_{20}$ alkylene divalent radicals; and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The one or more alkoxysilanes comprising at least one solubilizing functional group may also be chosen from compounds of the following formula:

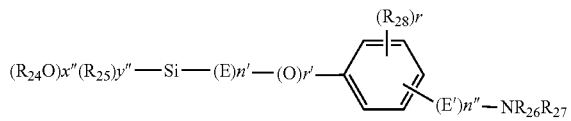

wherein $R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x" is 2 or 3; [0170] y" is 3-x";

n' is 0 or 1;

n" is 0 or 1;

E and E', which may be identical or different, are chosen from linear and branched $C_1$-$C_{20}$ alkylene divalent radicals;

$R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_1$-$C_{20}$ alcohol ester, amine, amide, carboxyl, alkoxysilane, hydroxyl, carbonyl, and acyl groups;

r is an integer ranging from 0 to 4;

r'=0 or 1; and $R_{28}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

According to a further exemplary embodiment, one or more alkoxysilanes comprising at least one solubilizing functional group may be chosen from compounds of the following formula:

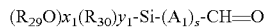

wherein $R_{29}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

$x_1$ is 2 or 3;

$y_1$ is 3-$x_1$;

$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_8$-$C_{30}$ aryl, hydroxyl, and carbonyl groups; and s is 0 or 1.

In some instances, one or more alkoxysilanes comprising at least one solubilizing functional group is chosen from compounds of the following formula:

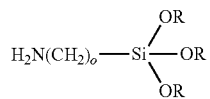

wherein the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom in a formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein. Other useful alkoxysilanes are cited, for example, in EP1216022, incorporated by reference herein, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST. In some cases, the alkoxysilanes may comprise at least one hydrocarbon chain containing fluorine atoms. Non-limiting examples include but are not limited to the 3,3,3-trifluoropropyltriethoxysilane or tridecafluorooctyltriethoxysilane compounds described in EP1510197, incorporated by reference herein.

It is also contemplated that these alkoxysilanes may carry a solubilizing, non-hydrolysable group such as amino groups, carboxylic acids, sulphonic acids, sulphates, quaternary ammoniums, polyalcohols, polyether and phosphates. One possible example of the foregoing types of alkoxysilanes is aminopropyl-N-(4,2-dinitrophenyl)aminopropyldiethoxysilane. Additional exemplary compounds of this type are described, for example, in EP1216023, which is herein incorporated by reference. Non-limiting examples of useful alkoxysilanes include 3-mercaptopropyltriethoxysilane and aminoalkyltrialkoxysilanes such as 3-aminopropyltriethoxysilane ("APTES", described in French Patent Application No. FR 2 789 896, incorporated herein by reference), and mixtures thereof. In some cases, the hair-treatment compositions include 3-aminopropyltriethoxysilane.

Cationic Polymers

Non-limiting examples of cationic polymers include poly(methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may be chosen from optionally polyoxyalkylenated, primary, secondary or tertiary fatty amines, or salts thereof, and quaternary ammonium salts, and a mixture thereof.

The fatty amines generally comprise at least one $C_8$-$C_{30}$ hydrocarbon-based chain.

Examples of quaternary ammonium salts that may especially be mentioned include: those corresponding to the general formula (III) below:

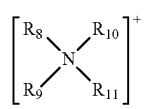

(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; X is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (IV) below:

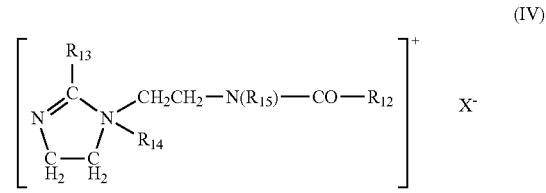

(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Evonik;

B. a quaternary diammonium or triammonium salt, in particular of formula (V):

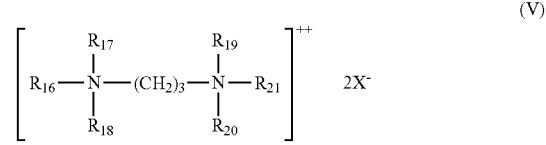

(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, FINQUAT CT-P, sold by the company Innospec (Quaternium 89), and FINQUAT CT, sold by the company Innospec (Quaternium 75), C. a quaternary ammonium salt containing at least one ester function, such as those of formula (VI) below:

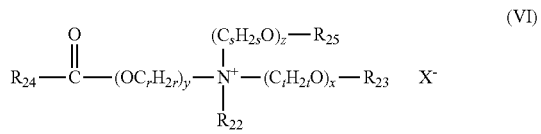

in which:

$R_{22}$ is chosen from $C_1$-$C_6$ alkyl groups and $C_1$-$C_6$ hydroxyalkyl or dihydroxyalkyl groups;

$R_{23}$ is chosen from:

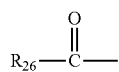

$R_{27}$, which is a linear or branched, saturated or unsaturated $C_1$-$C_{22}$ hydrocarbon-based group, and a hydrogen atom, $R_{25}$ is chosen from:

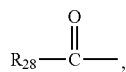

$R_{29}$, which is a linear or branched, saturated or unsaturated $C_1$-$C_6$ hydrocarbon-based group, and a hydrogen atom, $R_{24}$, $R_{26}$ and $R_{28}$, which may be identical or different, chosen from linear or branched, saturated or unsaturated $C_7$-$C_{21}$ hydrocarbon-based groups;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or mineral anion;

with the proviso that the sum x+y+z is from 1 to 15, that when x is 0 then $R_n$ denotes $R_{27}$, and that when z is 0 then $R_{25}$ denotes $R_{29}$.

The alkyl groups $R_{22}$ may be linear or branched, and more particularly linear. In some cases, $R_{22}$ denotes a methyl, ethyl, hydroxyethyl or dihydroxypropyl group, and more particularly a methyl or ethyl group. Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms. When $R_{25}$ is an $R_{29}$ hydrocarbon-based group, it preferably contains 1 to 3 carbon atoms. Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion $X^-$ is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly, in the composition according to the invention, of the ammonium salts of formula (VI) in which:

$R_{22}$ denotes a methyl or ethyl group, x and y are equal to 1;

z is equal to 0 or 1;

r, s and t are equal to 2;

$R_{23}$ is chosen from:

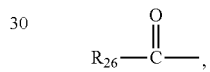

methyl, ethyl or $C_{14}$-$C_{22}$ hydrocarbon-based groups, and a hydrogen atom;

$R_{25}$ is chosen from:

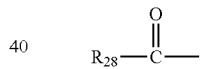

and a hydrogen atom;

$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups. The hydrocarbon-based groups are advantageously linear.

Mention may be made, for example, of the compounds of formula (VI) such as the diacyloxyethyldimethylammonium, diacylo xyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and a mixture thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names DEHYQUART by the company BASF, STEPANQUAT by the company Stepan, NOXAMIUM by the company Ceca or REWOQUAT WE 18 by the company Evonik.

Fatty Compounds

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

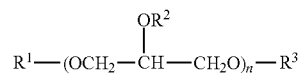

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substitued fatty acids, and a mixture thereof. Nonlimiting examples of fatty acid derivatives inlcude ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher metling point fatty compounds may also be used, for example, fatty compounds having a metling point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Polyurethane Latex Polymers

Polyurethane latex polymers that be used in the instant hair-treatment compositions include, polyurethane latex polymers such as aqueous polyurethane dispersions comprising the reaction products of (i), (ii), and/or (iii), defined below.

Reaction product (i) may be any prepolymer according to the formula:

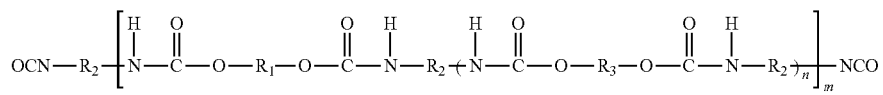

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecane¬dioic, 1,3-cyclohexanedicarboxylic, 1,4-cyclo¬hexane-dicarboxylic, 2,5-norboranedicarboxylic, diglycolic, thiodipropionic, 2,5-naphthalene-dicarboxylic, 2,6-naphthalene¬dicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythio-ether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexane-diol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanato-methyl-3,5,5-trimethylcyclohexane (isophorone diisocyanate or IPDI), bis(4-isocyanatocyclohexyl)-methane, 1,3-bis(isocyanatomethyl) cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxy-cyclo-hexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylol-butanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

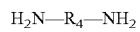

wherein $R_4$ is chosen from alkylene or alkylene oxide radicals, said radicals not being substituted with ionic or potentially ionic groups.

Reaction product (ii) may optionally be chosen from alkylene diamines, such as hydrazine, ethylene-diamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophorone-diamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

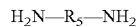

wherein $R_5$ is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, $R_5$ represents an alkylene radical substituted with sulphonic acid or sulphonate groups. By way of example only, the compound is chosen from sodium salts of N-(2-aminoethyl)-2-aminoethanesulphonic acid.

By way of non-limiting example, such polyurethane latex polymers include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989, and NEOREZ® R-2202).

Silicone-Organic Polymer Hybrid Compounds

Silicone-organic polymer hybrid compounds include silicone polyvinyl acetate compounds. The silicone-organic polymer hybrid compounds may also be chosen from a cross-linked anionic copolymer comprised of organic polymer blocks and silicone blocks, resulting in a multiblock polymer structure. The silicone-organic polymer hybrid compounds may be cross-linked anionic copolymers comprising at least one cross-linked polysiloxane structural unit. Examples of these polymers are described in PCT publication WO2011069786, which is incorporated herein by reference in its entirety.

In some cases, a particularly useful silicone-organic polymer hybrid compound is the compound having the INCI name of crotonic acid/vinyl C8-12 isoalkyl esters/VA/bis-vinyldimethicone crosspolymer, which is a copolymer of crotonic acid, vinyl C8-12 isoalkyl esters and vinyl acetate crosslinked with bis-vinyldimethicone. This compound is commercially available from the company Wacker Chemie AG under the tradename WACKER BELSI P1101 (may also be known under the tradename Wacker BELSIL P101). Crotonic acid/vinyl C8-12 isoalkyl esters/VA/bis-vinyldimethicone crosspolymer is also known by the technical name of crotonic acid/vinyl C8-12 isoalkyl esters/VA/divinyldimethicone crosspolymer.

Silicones

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)). Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or a mixture thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

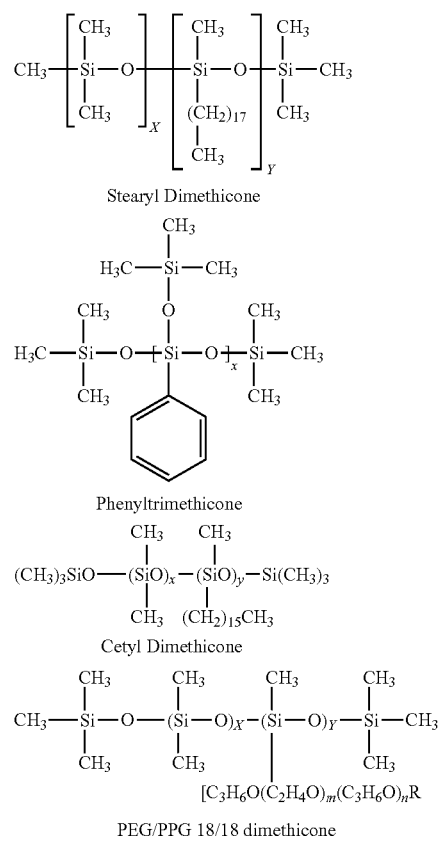

Stearyl Dimethicone

Phenyltrimethicone

Cetyl Dimethicone

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

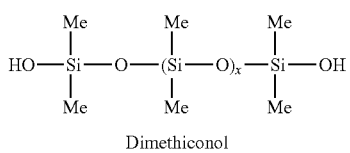

Dimethiconol

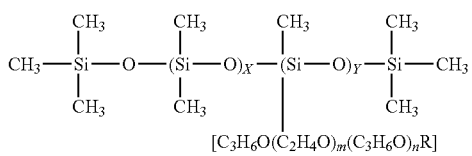

PEG/PEG 18/18 Dimethicone

X, y, m, and n are as defined above, and R is a $C_1$ to $C_{10}$ alkyl.

Another type of specific non limiting volatile silicone is a volatile short chain linear alkylmethylsilicone fluid. The volatile short chain linear alkylmethylsilicone fluid has the formula:

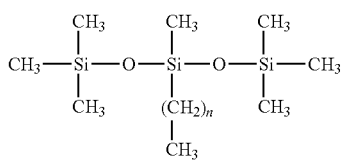

In the above formula, the integer represented by n has a value of five to twelve. Preferably, n has a value of five to eight. Compounds include, for example, 3-hexyl-1,1,1,3,5,5,5,-heptamethyltrisiloxane and 3-octyl-1,1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

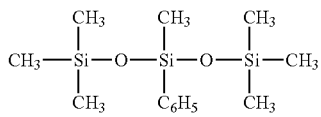

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula $[(Me_2)SiO]_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:
a) polysiloxanes corresponding to formula (A):

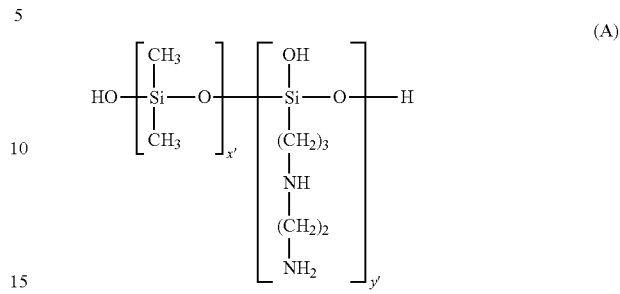

(A)

in which x' and y' are integers such that the weight-average molecular weight (Mw) is comprised between about 5000 and 500 000 b) amino silicones corresponding to formula (B):

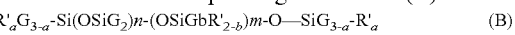

(B)

in which:
G, which may be identical or different, designate a hydrogen atom, or a phenyl, OH or $C_1$-$C_8$ alkyl group, for example methyl, or $C_1$-$C_8$ alkoxy, for example methoxy,
a, which may be identical or different, denote the number 0 or an integer from 1 to 3, in particular 0;
b denotes 0 or 1, and in particular 1;
m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;
R', which may be identical or different, denote a monovalent radical having formula —$C_qH_{2q}L$ in which q is a number ranging from 2 to 8 and L is an optionally quaternized amino group chosen from the following groups:
—NR"-Q-N(R")$_2$
—N(R")$_2$
—N+(R")$_3$ A-
—N+H(R")$_2$ A-
—N+H$_2$(R") A-
—N(R")-Q-N+R"H$_2$ A-
—NR"-Q-N+(R")$_2$H A-
—NR"-Q-N+(R")$_3$ A-,
in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

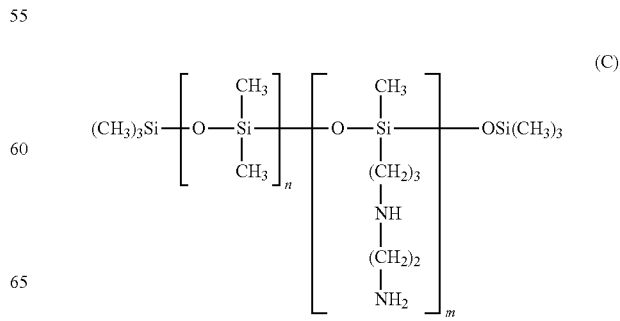

(C)

in which n and m have the meanings given above, in formula B.

Another group of amino silicones corresponding to this definition is represented by silicones having the following formulae (D) or (E):

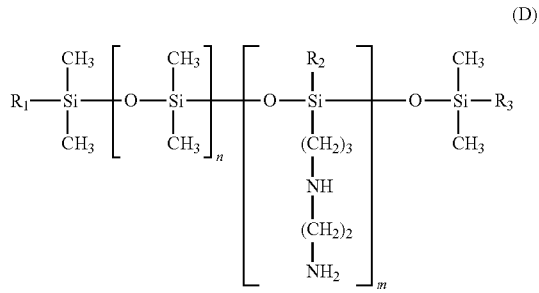

(D)

in which:
- m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and form to denote a number from 1 to 1000 and in particular from 1 to 10, and more particularly from 1 to 5;
- $R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

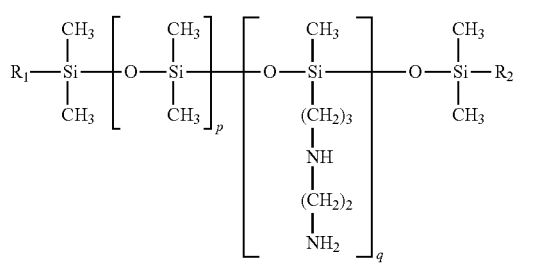

(E)

in which:
p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;
$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

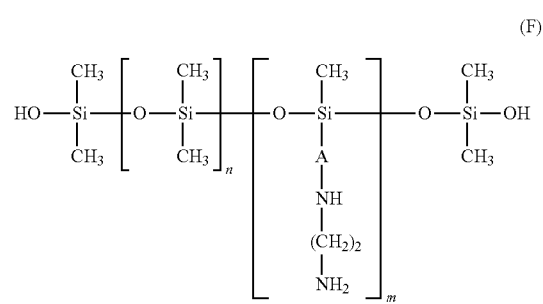

(F)

in which:
m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

$$\text{H}_3\text{C}-\underset{\underset{\text{CH}_3}{|}}{\overset{\overset{\text{CH}_3}{|}}{\text{Si}}}-\left[\text{O}-\underset{\underset{\text{CH}_3}{|}}{\overset{\overset{\text{CH}_3}{|}}{\text{Si}}}\right]_n-\left[\text{O}-\underset{\underset{\underset{\underset{\text{NH}_2}{|}}{\overset{(\text{CH}_2)_2}{|}}}{\overset{\overset{\text{NH}}{|}}{\overset{\overset{\text{A}}{|}}{\text{Si}}}}}{\overset{\overset{\text{CH}_3}{|}}{\phantom{.}}}\right]_m-\text{O}-\underset{\underset{\text{CH}_3}{|}}{\overset{\overset{\text{CH}_3}{|}}{\text{Si}}}-\text{CH}_3 \quad (G)$$

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

$$(R_5)_3-\text{Si}-\text{O}-\left[\underset{\underset{R_5}{|}}{\overset{\overset{R_5}{|}}{\text{Si}}}-\text{O}\right]_r-\left[\underset{\underset{R_5}{|}}{\overset{\overset{R_6-\text{CH}_2-\text{CHOH}-\text{CH}_2-\text{N}^+(R_5)_3 \quad Q^-}{|}}{\text{Si}}}-\text{O}\right]_s-\text{Si}-(R_5)_3 \quad (H)$$

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{15}$ alkylene radical or a divalent $C_1$-$C_{15}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

d) quaternary ammonium silicones having formula (I):

$$R_8-\underset{\underset{R_7}{|}}{\overset{\overset{R_7}{|}}{\text{N}^+}}-\text{CH}_2-\underset{}{\overset{\overset{\text{OH}}{|}}{\text{CH}}}-\text{CH}_2-R_6-\left[\underset{\underset{R_7}{|}}{\overset{\overset{R_7}{|}}{\text{Si}}}-\text{O}\right]_r-\underset{\underset{R_7}{|}}{\overset{\overset{R_7}{|}}{\text{Si}}}-R_6-\text{CH}_2-\underset{}{\overset{\overset{\text{OH}}{|}}{\text{CH}}}-\text{CH}_2-\underset{\underset{R_7}{|}}{\overset{\overset{R_7}{|}}{\text{N}^+}}-R_8 \quad 2X^- \quad (I)$$

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;

X- is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

$$\text{H}_2\text{N}-(C_mH_{2m})-\text{NH}-(C_nH_{2n})-\text{Si}-\left[\text{O}-\left[\underset{\underset{R_2}{|}}{\overset{\overset{R_1}{|}}{\text{Si}}}-\text{O}\right]_x-\underset{\underset{R_4}{|}}{\overset{\overset{R_3}{|}}{\text{Si}}}-R_5\right]_3 \quad (J)$$

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

[—(SiMe$_2$O)$_x$SiMe$_2$-R—N(R")—R'O(C$_2$H$_4$O)$_a$
(C$_3$H$_6$O)$_b$—R'—N(H)—R—]

or alternatively

[—(SiMe$_2$O)$_x$SiMe$_2$-R—N(R")—R'—O(C$_2$H$_4$O)$_a$
(C$_3$H$_6$O)$_b$—]

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

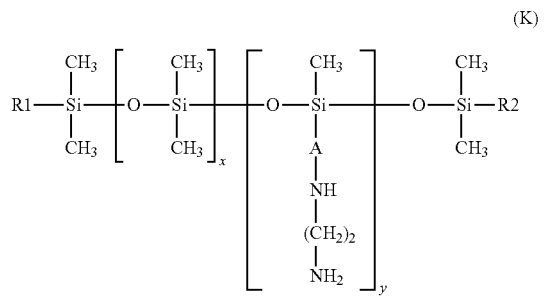

in which:

x and y are numbers ranging from 1 to 5000; preferably, x ranges from 10 to 2000 and especially from 100 to 1000; preferably, y ranges from 1 to 100;

$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$— and —$CH_2CH(CH_3)CH_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:

x ranging from 10 to 2000 and especially from 100 to 1000;

y ranging from 1 to 100;

A comprising 3 to 6 carbon atoms and especially 4 carbon atoms; preferably, A is branched; and more particularly A is chosen from the following divalent radicals: $CH_2CH_2CH_2$ and —$CH_2CH(CH_3)CH_2$—; and $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

Preferably, the amino silicones according to the invention are chosen from the amino silicones of formula (F). A preferred silicone of formula (F) is amodimethicone (INCI name) sold under the tradename XIAMETER® MEM-8299 Cationic Emulsion by Dow Corning.

Thickening Agents

Thickening agents (also referred to as thickeners or viscosity modifying agents) are well known. Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition. In some cases, associative thickening polymers may be useful in anionic surfactant-free hair-treatment compositions, in particular, anionic surfactant free conditioning shampoos. For example, the anionic surfactant-free conditioning shampoos may include one or more anionic associative polymers.

Film-Forming Polymers

Non-limiting examples of film-forming polymers include synthetic polymers (such as free-radical polymers and polycondensate polymers), and polymers of natural origin. Film-forming free-radical polymers may be vinyl polymers and vinyl copolymers, such as for example, acrylic polymers. The vinyl polymers may result from the polymerization of at least one monomer chosen from monomers with ethylenic unsaturation containing at least one acid group, esters of these acid monomers and amides of these acid monomers.

As a monomer with ethylenic unsaturation having at least one acid group, it is possible to use α,β-ethylenic unsaturated carboxylic acids chosen, for example from acrylic acid, methacrylic acid, crotonic acid, maleic acid and itaconic acid. In one embodiment of the invention, (meth) acrylic acid and crotonic acid may be used, and in another embodiment, (meth)acrylic acid may be used.

The esters of acid monomers may be chosen, for example, from (meth)acrylic acid esters (also called (meth)acrylates), for example, alkyl (meth)acrylates, wherein the alkyl group is chosen from linear, branched, and cyclic ($C_1$-$C_{30}$) alkyls, such as for example, ($C_1$-$C_{20}$)alkyl (meth)acrylates, and further still ($C_6$-$C_{10}$) aryl (meth)acrylates, and hydroxyalkyl (meth)acrylates, such as, ($C_2$-$C_6$) hydroxyalkyl (meth)acrylates.

Non-limiting examples of alkyl (meth)acrylates which may be mentioned are those chosen from methyl methacrylate, ethyl methacrylate, butyl methacrylate, isobutyl methacrylate, 2-ethylhexyl methacrylate, lauryl methacrylate and cyclohexyl methacrylate. Non-limiting examples of hydroxyalkyl (meth)acrylates which may be mentioned are those chosen from hydroxyethyl acrylate, 2-hydroxypropyl acrylate, hydroxyethyl methacrylate and 2-hydroxypropyl methacrylate. Non-limiting examples of aryl (meth)acrylates which may be mentioned are those chosen from benzyl acrylate and phenyl acrylate. The (meth)acrylic acid esters may be formed, for example, from ($C_1$-$C_{30}$) alkyl (meth) acrylates. The alkyl group of the esters may be chosen, for example, from fluorinated and perfluorinated alkyl groups, that is to say that some or all of the hydrogen atoms of the alkyl group may be substituted with fluorine atoms.

Non-limiting examples of amides of acid monomers which may be mentioned are those chosen from (meth) acrylamides, for example, N-alkyl(meth)acrylamides, such as, ($C_2$-$C_{12}$) alkyls. Non-limiting examples of N-alkyl(meth) acrylamides, which may be further mentioned are those chosen from N-ethylacrylamide, N-t-butylacrylamide, N-t-octylacrylamide and N-undecylacrylamide.

The vinyl polymers of the at least one film-forming polymer may also result from the homopolymerization or copolymerization of at least one monomer chosen from vinyl esters and styrene monomers. For example, these monomers may be polymerized with at least one acid monomer, esters thereof, and amides thereof, such as those mentioned above. Non-limiting examples of vinyl esters which may be mentioned are those chosen from vinyl acetate, vinyl neodecanoate, vinyl pivalate, vinylbenzoate and vinyl t-butyl benzoate.

Styrene monomers which may be mentioned are chosen, for example, from styrene and α-methylstyrene.

Non-limiting representatives of acrylic film-forming polymers include those sold under the names NEOCRYL XK-90, NEOCRYL A-1070, NEOCRYL A-1090, NEOCRYL BT-62, NEOCRYL A-1079, and NEOCRYL A-523 by the company Avecia-Neoresins, DOW LATEX 432 by the company Dow Chemical, and DAITOSOL 5000 AD by the company Daito Kasey Kogyo.

Non-limiting film-forming polymers also include at least one polycondensate chosen, for example, from polyesters, polyester amides, polyesters with at least one fatty chain, polyamides and epoxy ester resins.

In some instances, the at least one film-forming polymer is chosen from vinyl polymers, polyesters and polyamides.

The polyesters may be obtained, in a known manner, by polycondensation of at least one dicarboxylic acid with polyols, such as for example, diols.

The at least one dicarboxylic acid may be chosen, for example, from aliphatic dicarboxylic acids, alicyclic dicarboxylic acids and aromatic dicarboxylic acids. There may be mentioned as examples of such acids those chosen from: oxalic acid, malonic acid, dimethylmalonic acid, succinic acid, glutaric acid, adipic acid, pimelic acid, 2,2-dimethylgutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers may be used alone or in combination with at least two dicarboxylic acid monomers. In one embodiment of the invention, these monomers may be chosen, for example, from phthalic acid, isophthalic acid, and terephthalic acid.

Non-limiting representatives of diols may be chosen, for example, from aliphatic diols, alicyclic diols, and aromatic diols. In one embodiment of the invention the diols may be chosen, for example, from: ethylene glycol, diethylene glycol, triethylene glycol, 1,3-propanediol, cyclohexanedimethanol and 4-butanediol. Other non-limiting examples of polyols may be chosen, for example, from glycerol, pentaerythritol, sorbitol, and trimethylolpropane.

The polyester amides may be obtained in a manner similar to the polyesters, by polycondensation of diacids with a nitrogen containing compound chosen, for example, from diamines and amino alcohols. Non-limiting representatives of diamines may be chosen, for example, from ethylenediamine, hexamethylene-diamine, meta-phenylenediamine and para-phenylenediamine. A non-limiting example of an aminoalcohol which may be used is monoethanolamine.

The polyesters may also comprise at least one monomer carrying at least one group —$SO_3$ M, wherein M is chosen, for example, from a hydrogen group, an ammonium ion $NH_4^+$ and a metal ion chosen, for example, from $Na^+$, $Li^+$, $K^+$, $Mg^{2+}$, $Ca^{2+}$, $Cu^{2+}$, $Fe^{2+}$ and $Fe^{3+}$ ions. A bifunctional aromatic monomer comprising a group —$SO_3$ M may also be used, for example.

The aromatic ring of the bifunctional aromatic monomer also bearing a group —$SO_3$ M as described above may be chosen, for example, from benzene, naphthalene, anthracene, diphenyl, oxydiphenyl, sulphonyldiphenyl and methylenediphenyl rings. Examples of bifunctional aromatic monomers also bearing a group —SO3 M which may be mentioned include: sulphoisophthalic acid, sulphoterephthalic acid, sulphophthalic acid, and 4-sulphonaphthalene-2,7-dicarboxylic acid.

In the compositions according to the invention, it is possible to use copolymers based on isophthalate/sulphoisophthalate, such as for example, copolymers obtained by condensation of diethylene glycol, cyclohexanedimethanol, isophthalic acid and sulphoisophthalic acid. Such polymers are sold, for example, under the trade name EASTMAN AQ by the company Eastman Chemical Products.

The film-forming polymer of natural origin, which can be optionally modified, may be chosen, for example, from shellac resin, sandarac gum, dammars, elemis, copals, and water-insoluble cellulosic polymers.

Non-limiting examples of polymers formed from free-radical polymerization of at least one free-radical monomer located inside and/or partially at the surface, of preexisting particles of at least one polymer chosen, for example, from polyureas, polyesters, polyester amides and alkyds. These polymers are generally called "hybrid polymers."

In some cases, nonionic and/or amphoteric film-forming polymers may be useful. Non-limiting examples of nonionic film-forming polymers include vinylpyrrolidone homopolymers; copolymers of vinylpyrrolidone and of vinyl acetate; polyalkyloxazolines, such as the polyethyloxazolines provided by the company Polymer Chemistry Innovations under the names AQUAZOL HP, and AQUZOL HVIS; vinyl acetate homopolymers, such as the product provided under the name UCAR 130 Latex Resin by the company Dow Chemical or the product provided under the name ULTRAPURE POLYMER 2041-R 012 by the company Ultra Chemical, Inc.; copolymers of vinyl acetate and of acrylic ester, such as the product provided under the name RHODOPAS AD 310 from Rhone-Poulenc; copolymers of vinyl acetate and of ethylene, such as the product provided under the name DERMACRYL LOR by the company Akzo Nobel; copolymers of vinyl acetate and of maleic ester, for example of dibutyl maleate, such as the product provided under the name APPRETAN MB Extra by the company Clariant; copolymers of polyethylene and of maleic anhydride; alkyl acrylate homopolymers and alkyl methacrylate homopolymers, such as the product provided under the name MICROPEARL RQ 750 by the company Matsumoto or the product provided under the name LUHYDRAN A 848 S by the company BASF; acrylic ester copolymers, such as, for example, copolymers of alkyl acrylates and of alkyl methacrylates, such as the product provided by the company Dow Chemical under the name PRIMALAC-261 K and the product provided by Evonik under the name Eudragit NE 30 D, by the company BASF under the names ACRONAL 601, LUHYDRAN R 8833 or 8845, or by the company Clariant under the names APPRETAN N 9213 or N9212; copolymers of acrylonitrile and of a non-ionic monomer chosen, for example, from butadiene and alkyl (meth)acrylates; mention may be made of the products provided under the names NIPOL LX 531 B by the company Nippon Zeon or those provided under the name CJ 0601 B by the company Rohm and Haas; copolymers of alkyl acrylate and of urethane, such as the product 8538-33 by the company National Starch; polyamides, such as the product ESTAPOR LO 11 provided by the company Rhone-Poulenc; and chemically modified or unmodified non-ionic guar gums.

The unmodified non-ionic guar gums are, for example, the products sold under the name VIDOGUM GH by the company Unipectine and under the name JAGUAR S by the company Rhodia. The modified non-ionic guar gums, which can be used according to the invention, are preferably modified by C1-C6 hydroxyalkyl groups. Mention may be made, by way of example, of the hydroxymethyl, hydroxyethyl, hydroxypropyl, and hydroxybutyl groups. These guar gums are well known in the state of the art and can, for example, be prepared by reacting the corresponding alkene oxides, such as, for example, propylene oxides, with guar gum, so as to obtain a guar gum modified by hydroxypropyl groups.

Other nonionic film forming polymers may be chosen from non-ionic guar gums optionally modified by hydroxyalkyl groups are, for example, sold under the trade names JAGUAR HP8, JAGUAR HP60, JAGUAR HP120, and JAGUAR HP 105 by the company Rhodia or under the name GALACTASOL 4H4FD2 by the company Ashland Specialty Ingredients.

The alkyl radicals of the non-ionic fixing polymers have from 1 to 6 carbon atoms, unless otherwise mentioned.

Other suitable examples of film forming polymers are fixing polymers of grafted silicone type comprising a polysiloxane portion and a portion composed of a non-silicone organic chain, one of the two portions constituting the main chain of the polymer and the other being grafted onto the said main chain. These polymers can be non-ionic.

Preferred nonionic film forming polymers of the present disclosure are chosen from vinylpyrrolidone homopolymers and copolymers of vinylpyrrolidone and of vinyl acetate. Vinylpyrrolidone homopolymers (INCI name: polyvinylpyrrolidone) are commercially available from Ashland Specialty Ingredients under the tradename PVP K. Copolymers of vinylpyrrolidone and of vinyl acetate (INCI name: VP/VA copolymer) are commercially available from BASF under the tradename LUVISKOL VA.

Non-limiting examples of amphoteric film-forming polymers include those containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers; B and C can also denote a cationic polymer chain containing primary, secondary, tertiary or quaternary amine groups, in which at least one of the amine groups bears a carboxylic or sulphonic group connected via a hydrocarbon radical or alternatively B and C form part of a chain of a polymer containing an α,β-dicarboxylic ethylene unit in which one of the carboxylic groups has been made to react with a polyamine containing one or more primary or secondary amine groups.

The amphoteric film-forming polymers corresponding to the definition given above which are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537, which is incorporated herein by reference in its entirety.

(2) polymers containing units derived from:

a) at least one monomer chosen from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

In some cases, the preferred basic comonomers are aminoethyl, butylaminoethyl, N,N'-dimethylaminoethyl and N-tert-butylaminoethyl methacrylates. For example, octylacrylamide/acrylates/butylaminoethyl methacrylate copolymer such as the products sold under the name AMPHOMER or Balance 47 (formerly LOVOCRYL 47) by the company Akzo Nobel may be useful.

(3) crosslinked and alkylated polyamino amides partially or totally derived polyamino amides.

(4) polymers containing zwitterionic units of formula:

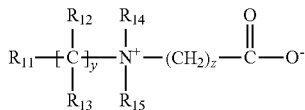

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or methyl, ethyl or propyl, and R14 and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate. By way of example, mention may be made of the copolymer of methyl methacrylate/dimethyl carboxymethylammonio methyl ethylmethacrylate.

(5) Polymers derived from chitosan.

(6) Polymers derived from the N-carboxyalkylation of chitosan, such as N-carboxymethylchitosan or N-carboxybutylchitosan sold under the name "EVALSAN" by the company Jan Dekker.

(7) Polymers corresponding to the general formula below are described, for example, in French patent 1,400,366:

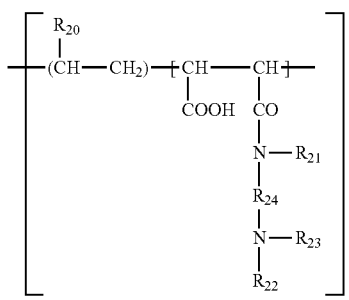

in which $R_{20}$ represents a hydrogen atom, a $C_{H3}O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: $—R_{24}—N(R_{22})_2$, $R_{24}$ representing a $—CH_2—CH_2$, $—CH_2—CH_2—CH_2—$ or $—CH_2—CH(CH_3)—$ group, $R_{22}$ having the meanings mentioned above, as well as the higher homologues of these radicals and containing up to 6 carbon atoms.

(8) Amphoteric polymers of the type -D-X-D-X chosen from:

a) polymers obtained by the action of chloroacetic acid or sodium chloroacetate on compounds containing at least one unit of formula: -D-X-D-X-D- (I), where D denotes a radical

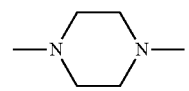

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) Polymers of formula: -D-X-D-X— (I'), in which D denotes a radical

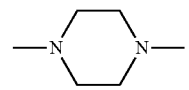

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) (C1-05)alkyl vinyl ether/maleic anhydride copolymers, the maleic anhydride being partially modified by semiamidation with an N,N-dialkylaminoalkylamine such as N,N-dimethyl-aminopropylamine or by semiesterification with an N,N-dialkanolamine. These copolymers can also contain other vinyl comonomers such as vinylcaprolactam.

Implementation of the present disclosure is provided by way of the following examples. The examples serve to illustrate the technology without being limiting in nature.

Example 1

Testing was carried out to determine the influence of various routines for treating chemically relaxed hair. The chemical relaxer composition, the hair-treatment compositions, the conditioning compositions, and the auxiliary composition used in the testing are described in the below tables.

Chemical Relaxer Composition

| | INCI US Name | wt. % |
|---|---|---|
| Active | SODIUM HYDROXIDE (100%) | 2.1 |
| Fatty Compounds | PETROLEUM JELLY, COCOA BUTTER, MINERAL OIL, AND/OR SHEA BUTTER | 36 |
| Surfactants | PEG-75 LANOLIN, CETEARYL ALCOHOL, BEHENTRIMONIUM METHOSULFATE, AND/OR POLYSORBATE 60 | 12.8 |
| Cationic Polymer | POLYQUATERNIUM-6 | 0.5 |
| Solvent | PROPYLENE GLYCOL | 3 |
| Fragrance | OPTIONAL COMPONENT | 0-2 |
| Water | WATER | Q.S |

Hair-Treatment Compositions

| | INCI US | #1 | #2 | #3 | #4 |
|---|---|---|---|---|---|
| Dicarboxylic Acid | MALEIC ACID | 10.7 | 9.6 | | |
| | MALONIC ACID | | | 9.6 | 9.6 |
| Alkanolamine | MONOETHANOLAMINE | 5.4 | 2.5 | 4.1 | 2.5 |
| Alkoxysilane | AMINOPROPYL TRIETHOXYSILANE | — | 2.5 | — | 2.5 |
| Cationic Polymer | POLYQUATERNIUM-6 | | 0.4 | | 0.4 |
| Dye(s) | OPTIONAL COMPONENT | 0-3 | 0-3 | 0-3 | 0-3 |
| Fragrance(s) | OPTIONAL COMPONENT | 0-3 | 0-3 | 0-3 | 0-3 |
| Water | WATER | Q.S. | Q.S. | Q.S. | Q.S. |

Conditioning Compositions

| | INCI US | A | B |
|---|---|---|---|
| Active | MALEIC ACID | 1.9 | |
| Active | MALONIC ACID | | 1.7 |
| Active | MONOETHANOLAMINE | 0.8 | |
| Cationic Surfactant(s) | QUATERNIUM-91, CETRIMONIUM CHLORIDE, STEARAMIDOPROPYL DIMETHYLAMINE, BEHENTRIMONIUM METHOSULFATE, AND/OR CETRIMONIUM METHOSULFATE | 1.9 | 1.9 |
| Fatty Compound(s) | CETEARYL ALCOHOL AND/OR MINERAL OIL | 4.3 | 4.3 |
| Cationic Polymer | POLYQUATERNIUM-37 | 0.2 | 0.2 |
| Water-Soluble Solvent(s) | GLYCERIN AND/OR PROPYLENE GLYCOL | 3.5 | 3.5 |
| Thickener(s) | OPTIONAL COMPONENT | 0-2 | 0-2 |
| Preservative(s) | OPTIONAL COMPONENT | 0-2 | 0-2 |
| Fragrance(s) | OPTIONAL COMPONENT | 0-2 | 0-2 |
| Water | WATER | Q.S | Q.S. |

Auxiliary Composition

| Component | INCI US Name | wt. % |
|---|---|---|
| Polyurethane | POLYURETHANE-34 | 1 |
| Silicone-Organic Polymer Hybrid Compound | CROTONIC ACID/VINYL C8-12 ISOALKYL ESTERS/VA/BIS-VINYLDIMETHICONE CROSSPOLYMER | 0.1 |
| Thickeners | HYDROXYPROPYL GUAR, HYDROXYETHYLCELLULOSE, AND/OR POTATO STARCH MODIFIED | 1.5 |
| Film Forming Polymer | VP/DIMETHYLAMINOETHYL-METHACRYLATE COPOLYMER | 0.6 |
| Cationic Polymer | POLYQUATERNIUM-11 | 0.2 |
| Silicone | DIMETHICONE, DIMETHICONOL, AND/OR PHENYL TRIMETHICONE | 19 |
| Solvent | ETHYLHEXYLGLYCERIN | 0.1 |
| Fragrance | OPTIONAL COMPONENT | 0-2 |
| Preservative | OPTIONAL COMPONENT | 0-2 |
| | WATER | Q.S. |

Hair swatches were treated with one of the following routines:

1. Hair swatches were treated with the chemical relaxer composition only. After chemically relaxing the hair, the chemical relaxer composition was rinsed from the hair and shampooed. The hair was blow dried an evaluated by experts.
2. Hair swatches were treated with the chemical relaxer composition followed by treatment with Formulation #1 (hair-treatment composition) and conditioning composition A. After rinsing the chemical relaxer composition from the hair, Formulation #1 (hair-treatment composition) was applied to the hair and allowed to remain on the hair for about 10 minutes. After allowing Formulation #1 to remain on the hair for about 10 minutes, without rinsing Formulation #1 from the hair, Conditioning Composition A was applied to the hair (Conditioning Composition A was layered onto the hair that was already covered with Formulation #1). Conditioning Composition A was then allowed to remain on the hair for 10 minutes. After Conditioning Composition A had remained on the hair for 10 minutes, Conditioning Composition A and Formulation #1 were rinsed from the hair. The hair was shampooed, blow dried, and evaluated by experts.
3. Hair swatches were treated with the chemical relaxer composition followed by treatment with Formulation #1 (hair-treatment composition), conditioning composition A, and the Auxiliary composition. After rinsing the chemical relaxer composition from the hair, Formulation #1 (hair-treatment composition) was applied to the hair and allowed to remain on the hair for about 10 minutes. After allowing Formulation #1 to remain on the hair for about 10 minutes, without rinsing Formulation #1 from the hair, Conditioning Composition A was applied to the hair (Conditioning Composition A was layered onto the hair that was already covered with Formulation #1). Conditioning Composition A was then allowed to remain on the hair for 10 minutes. After Conditioning Composition A had remained on the hair for 10 minutes, Conditioning Composition A and Formulation #1 were rinsed from the hair. After rinsing Conditioning Composition A and Formulation #1 from the hair, the Auxiliary Composition was combined with a shampoo (1:1 ratio) and applied to the hair (this combination was used to shampoo the hair). After rinsing the shampoo and auxiliary composition combination from the hair, the hair was blow dried and evaluated by experts.
4. Hair swatches were treated with the chemical relaxer composition followed by treatment with Formulation #3

(hair-treatment composition), conditioning composition B, and the auxiliary composition. After rinsing the chemical relaxer composition from the hair, Formulation #3 (hair-treatment composition) was applied to the hair and allowed to remain on the hair for about 10 minutes. After allowing Formulation #3 to remain on the hair for about 10 minutes, without rinsing Formulation #3 from the hair, Conditioning Composition B was applied to the hair (Conditioning Composition B was layered onto the hair that was already covered with Formulation #3). Conditioning Composition B was then allowed to remain on the hair for 10 minutes. After Conditioning Composition B had remained on the hair for 10 minutes, Conditioning Composition B and Formulation #3 were rinsed from the hair. After rinsing Conditioning Composition B and Formulation #3 from the hair, the Auxiliary Composition was combined with a shampoo (1:1 ratio) and applied to the hair (this combination was used to shampoo the hair). After rinsing the shampoo and auxiliary composition combination from the hair, the hair was blow dried and evaluated by experts.

5. Hair swatches were treated with the chemical relaxer composition followed by treatment with Formulation #4 (hair-treatment composition), conditioning composition B, and the auxiliary composition. After rinsing the chemical relaxer composition from the hair, Formulation #4 (hair-treatment composition) was applied to the hair and allowed to remain on the hair for about 10 minutes. After allowing Formulation #4 to remain on the hair for about 10 minutes, without rinsing Formulation #4 from the hair, Conditioning Composition B was applied to the hair (Conditioning Composition B was layered onto the hair that was already covered with Formulation #4). Conditioning Composition B was then allowed to remain on the hair for 10 minutes. After Conditioning Composition B had remained on the hair for 10 minutes, conditioning composition B and formulation #4 were rinsed from the hair. After rinsing Conditioning Composition B and Formulation #4 from the hair, the auxiliary composition was combined with a shampoo (1:1 ratio) and applied to the hair (this combination was used to shampoo the hair). After rinsing the shampoo and auxiliary composition combination from the hair, the hair was blow dried and evaluated by experts.

The panel of experts evaluated the hair swatches and the results are summarized in the table below, where "✓" represents a typical result for each attribute. "✓✓" represents an appreciable improvement in the attribute; and "✓✓✓" represents a significant (best) improvement in the attribute.

The results show that hair treated with a chemical relaxer composition, a hair-treatment composition, a conditioning composition, and an auxiliary composition exhibited the best attributes.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

| Attribute | Relaxer Alone | Relaxer Formulation 1 Conditioner A | Relaxer Formulation 1 Conditioner A Auxiliary | Relaxer Formulation 3 Conditioner B Auxiliary | Relaxer Formulation 4 Conditioner B Auxiliary |
|---|---|---|---|---|---|
| Straightness | ✓✓ | ✓✓ | ✓✓ | ✓✓ | ✓✓ |
| Strength | ✓ | ✓✓ | ✓✓ | ✓✓ | ✓✓ |
| Discipline | ✓ | ✓ | ✓✓ | ✓✓ | ✓✓✓ |
| Frizz-Reduction | ✓ | ✓ | ✓✓ | ✓✓ | ✓✓✓ |
| Style-Control | ✓ | ✓ | ✓✓ | ✓✓ | ✓✓✓ |
| Shine | ✓ | ✓ | ✓✓ | ✓✓ | ✓✓✓ |
| Smoothness | ✓ | ✓ | ✓✓ | ✓✓ | ✓✓✓ |
| Soft/suppleness | ✓ | ✓ | ✓✓ | ✓✓ | ✓✓✓ |
| Long-lastingness | ✓ | ✓ | ✓✓ | ✓✓ | ✓✓✓ |

The salts, for example, the salts of the amino acids, the amino sulfonic acids, and the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

Some of the various categories of components identified for the various composition described herein, including the hair-treatment compositions, may overlap. In such cases where overlap may exist between two or more components, a single overlapping compound does not represent more than one component. For example, a homopolymer of methyl quaternized dimethylaminoethyl methacrylate may be characterized as both a cationic polymer component and a thickening agent component. If a particular composition is described as including both a cationic polymer and a thickening agent, a single homopolymer of methyl quaternized dimethylaminoethyl methacrylate would serve as only the cationic polymer or only the thickening agent (the compound does not serve as both the cationic polymer and the thickening agent in the same composition).

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat," and its grammatical variations, relates to contacting hair with the hair-treatment compositions of the present disclosure.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for treating hair comprising:
   applying to the hair a hair-treatment composition comprising:
     at least 0.5 wt. %, based on the total weight of the hair-treatment composition, of at least one non-polymeric mono, di, or tricarboxylic acid, and/or a salt thereof;
     one or more amines selected from the group consisting of diamines, polyamines, alkylamines, alkanolamines, and/or a mixture thereof; and
     water;
   applying to the hair a conditioning composition comprising:
     one or more cationic surfactants; and
     one or more fatty compounds; and
   applying to the hair an auxiliary composition comprising:
     one or more polyurethane latex polymers.

2. A method of claim 1, wherein the hair-treatment composition and the auxiliary composition are applied to chemically relaxed hair.

3. A method of claim 2, wherein at least the hair-treatment composition is applied to the chemically relaxed hair within 30 minutes from when a chemical relaxer composition is rinsed from the hair.

4. A method of claim 1, wherein the hair-treatment composition is allowed to remain on the hair for about 10 seconds to about 30 minutes before being rinsed from the hair.

5. A method of claim 1, wherein the hair-treatment composition comprises at least 0.5 wt. % of at least one non-polymeric dicarboxylic acid, and/or a salt thereof.

6. A method of claim 5, wherein the at least one dicarboxylic acid and/or a salt thereof is selected from the group consisting of oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and a salt thereof.

7. A method of claim 6, wherein the dicarboxylic acid and/or a salt thereof is selected from the group consisting of malonic acid, maleic acid, and a salt thereof.

8. A method claim 1, wherein the hair-treatment composition comprises at least 0.5 to about 20 wt. % of at least one non-polymeric mono, di, or tricarboxylic acid and/or a salt thereof, based on the total weight of the hair-treatment composition.

9. A method of claim 1, wherein the hair-treatment composition comprises one or more alkylamines and/or alkanolamines selected from the group consisting of compounds of formula (II):

$$NR_3R_4R_5 \hspace{3cm} (II)$$

wherein $R_3$, $R_4$ and $R_5$ are independently H, $C_1$-$C_{40}$ alkyl, $C_1$-$C_{40}$ monohydroxyalkyl or C2-C40 polyhydroxyalkyl, provided that at least one of $R_3$, $R_4$ and $R_5$ is an alkyl or mono or polyhydroxyalkyl.

10. A method of claim 9, wherein the hair-treatment composition comprises one or more alkanolamines selected from the group consisting of monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof.

11. A method of claim 10, wherein the hair-treatment composition comprises monoethanolamine.

12. A method of claim 1, wherein the hair-treatment composition comprises about 1 to about 20 wt. % of the one or more amines, based on the total weight of the hair-treatment composition.

13. A method of claim 1, wherein the hair-treatment composition further comprises:
one or more cationic silicones, cationic silanes, cationic silane oligomers, or a mixture thereof.

14. A method of claim 13, wherein the one or more cationic silicones, cationic silanes, and cationic silane oligomers are selected from the group consisting of aminoalkyltrialkoxysilanes, an oligomer thereof, and a mixture thereof.

15. A method of claim 14 comprising 3-mercaptopropyltriethoxysilane and/or 3-aminopropyltriethoxysilane.

16. A method of claim 13, wherein the total amount of the one or more cationic silicones, cationic silanes, cationic silane oligomers, and a mixture thereof is about 0.1 to about 20 wt. %, based on the total weight of the hair-treatment composition.

17. A method of claim 1, wherein the hair-treatment composition further comprises:
one or more cationic polymers.

18. A method of claim 17, wherein the one or more cationic polymers comprises a polyquaternium.

19. A method of claim 18, wherein the one or more cationic polymers comprises polyquaternium-6.

20. A method of claim 17, wherein the hair-treatment composition comprises about 0.01 to about 10 wt. % of the one or more cationic polymers, based on the total weight of the hair-treatment composition.

21. A method of claim 1, wherein the auxiliary composition comprises one or more polyurethane latex polymers selected from the group consisting of polyurethane-32, polyurethane-34, polyurethane-35, polyurethane-48, and a mixture thereof.

22. A method of claim 1, wherein the auxiliary composition further comprises:
one or more thickening agents.

23. A method of claim 22, wherein the one or more thickening agents are selected from the group consisting of carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof.

24. A method claim 22, wherein the auxiliary composition comprises about 0.01 to about 10 wt. % of the one or more thickening agents, based on the total weight of the auxiliary composition.

25. A method of claim 1, wherein the auxiliary composition is:
mixed with a shampoo prior to application to hair;
layered onto hair with a shampoo;
applied to wet hair after a shampoo has been rinsed from the hair;
layered onto hair with a conditioner;
mixed with a conditioner prior to application to hair; and/or
applied to wet hair after a conditioner has been rinsed from the hair.

26. A method of claim 1 for treating chemically relaxed hair comprising:
applying the hair-treatment composition and the conditioning composition to the hair within 30 minutes of treating the hair with a chemical relaxing composition;
rinsing the hair-treatment composition and the conditioning composition of from the hair; and
applying the auxiliary composition to the hair within 30 minutes of rinsing of the hair-treatment composition and the conditioning composition from the hair.

27. A method of claim 26, wherein the hair-treatment composition is applied to the hair, and optionally rinsed from the hair, before the conditioning composition is applied to the hair.

28. A method of claim 26, wherein the hair-treatment composition is mixed with the conditioning composition before being applied to the hair.

29. A method of claim 26, wherein the hair-treatment composition is applied to the hair, and without first rinsing the hair-treatment composition from the hair, the conditioning composition is also applied to the hair.

30. A method of claim 26, wherein the conditioning composition is allowed to remain on the hair for about 10 seconds to about 30 minutes before being rinsed from the hair.

31. A method of claim 1, wherein the conditioning composition comprises one or more cationic surfactants selected from the group consisting of cetrimonium chloride, stearimonium chloride, behentrimonium chloride, behentrimonium methosulfate, behenamidopropyltrimonium methosulfate, stearamido-propyltrimonium chloride, arachidtrimonium chloride, distearyldimonium chloride, dicetyldimonium chloride, tricetylmonium chloride, oleamidopropyl dimethylamine, linoleamidopropyl dimethylamine, iso stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof.

32. A method of claim 1, wherein the conditioning composition comprises about 0.1 to about 15 wt. % of the one or more cationic surfactants, based on the total weight of the conditioning composition.

33. A method of claim 1, wherein the conditioning composition comprises one or more fatty compounds selected from the group consisting of oils, waxes, butter, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof.

34. A method of claim 1, wherein the conditioning composition comprises about 1 to about 40 wt. % of the one or more fatty compounds, based on the total weight of the conditioning composition.

35. A method of claim 1, wherein the conditioning composition further comprises:
   at least 0.5 wt. % of at least one non-polymeric mono, di, or tricarboxylic acid, and/or a salt thereof, based on the total weight of the hair-treatment composition;
   wherein the at least one non-polymeric mono, di, or tricarboxylic acid, and/or a salt thereof in the conditioning composition may be the same or different than the at least one non-polymeric mono, di, or tricarboxylic acid, and/or a salt in the hair-treatment composition.

36. A method of claim 1, wherein treating the hair comprises:
   conditioning the hair;
   providing frizz control to the hair;
   improving ease of combability and detangling;
   increasing the appearance of hair volume;
   protecting the hair from damage;
   repairing damaged hair;
   strengthening the hair;
   imparting softness to the hair; and/or
   improving the hair's shine and luster.

* * * * *